United States Patent
Ikenaga

(10) Patent No.: US 9,545,190 B2
(45) Date of Patent: Jan. 17, 2017

(54) ENDOSCOPE APPARATUS WITH ROTATABLE IMAGING MODULE

(71) Applicant: Sony Corporation, Tokyo (JP)

(72) Inventor: Yuichiro Ikenaga, Kanagawa (JP)

(73) Assignee: Sony Corporation, Tokyo (JP)

( * ) Notice: Subject to any disclaimer, the term of this patent is extended or adjusted under 35 U.S.C. 154(b) by 131 days.

(21) Appl. No.: 14/174,592

(22) Filed: Feb. 6, 2014

(65) Prior Publication Data

US 2014/0228644 A1  Aug. 14, 2014

(30) Foreign Application Priority Data

Feb. 14, 2013  (JP) .................................. 2013-026351

(51) Int. Cl.
*A61B 1/05* (2006.01)
*A61B 1/00* (2006.01)
*G02B 23/24* (2006.01)

(52) U.S. Cl.
CPC ....... *A61B 1/00193* (2013.01); *A61B 1/00183* (2013.01); *A61B 1/051* (2013.01); *A61B 1/00181* (2013.01); *G02B 23/2415* (2013.01)

(58) Field of Classification Search
CPC ............ A61B 1/00193; A61B 1/00181; A61B 1/00174; G02B 23/2415
See application file for complete search history.

(56) References Cited

U.S. PATENT DOCUMENTS

| | | | |
|---|---|---|---|
| 5,368,015 A * | 11/1994 | Wilk ................. | A61B 1/00147 128/903 |
| 5,436,655 A * | 7/1995 | Hiyama ................ | A61B 1/063 348/139 |
| 5,557,454 A * | 9/1996 | Takahashi .......... | A61B 1/00193 348/45 |

(Continued)

FOREIGN PATENT DOCUMENTS

| | | | | |
|---|---|---|---|---|
| IL | WO 2009144729 A1 * | 12/2009 | ............... | A61B 1/04 |
| JP | S63-294508 | 12/1988 | | |

(Continued)

OTHER PUBLICATIONS

Official Action (with English translation) for Japanese Patent Application No. 2013-026351 mailed Apr. 21, 2015, 11 pages.

(Continued)

*Primary Examiner* — John P Leubecker
(74) *Attorney, Agent, or Firm* — Sheridan Ross P.C.

(57) ABSTRACT

An endoscope including a lens barrel in which a partial region including at least a distal end is inserted inside a body cavity of a person under measurement, an imaging module is provided in the distal end of the lens barrel, and the imaging module having at least one pair of image sensors arranged in parallel at a mutually prescribed distance are described. The imaging module may be switched between a storage state in which the imaging module is stored within the lens barrel in a manner that an extension direction of imaging surfaces of the image sensors becomes a direction along a first direction, and a photographing state in which (Continued)

the imaging module is projected outside of the lens barrel in a manner that the extension direction of the imaging surfaces of the image sensors becomes a direction along a second direction.

9 Claims, 10 Drawing Sheets

(56) References Cited

U.S. PATENT DOCUMENTS

| | | | | |
|---|---|---|---|---|
| 5,743,846 | A * | 4/1998 | Takahashi | G02B 23/2415 600/111 |
| 7,751,870 | B2 * | 7/2010 | Whitman | A61B 1/313 600/104 |
| 2002/0007110 | A1 * | 1/2002 | Irion | A61B 1/00181 600/170 |
| 2004/0070667 | A1 * | 4/2004 | Ando | H04N 13/0022 348/46 |
| 2005/0038317 | A1 * | 2/2005 | Ratnakar | A61B 1/00105 600/101 |
| 2006/0149129 | A1 * | 7/2006 | Watts | A61B 1/00135 600/113 |
| 2007/0293720 | A1 * | 12/2007 | Bayer | A61B 1/00096 600/112 |
| 2009/0187072 | A1 * | 7/2009 | Manohara | A61B 1/00039 600/109 |
| 2010/0249512 | A1 * | 9/2010 | McKinley | A61B 17/3421 600/160 |
| 2011/0230894 | A1 * | 9/2011 | Simaan | A61B 1/00183 606/130 |
| 2011/0306832 | A1 * | 12/2011 | Bassan | A61B 1/00009 600/109 |
| 2013/0010065 | A1 * | 1/2013 | Song | A61B 1/00193 348/45 |

FOREIGN PATENT DOCUMENTS

| | | |
|---|---|---|
| JP | H04-500768 | 2/1992 |
| JP | H05-115425 | 5/1993 |
| JP | H06-261860 | 9/1994 |
| JP | 2004-305525 | 11/2004 |
| JP | 2007-532240 | 11/2007 |
| JP | 2013-085615 | 5/2013 |
| WO | WO 99/00049 | 1/1991 |
| WO | WO 2013/054944 | 4/2013 |

OTHER PUBLICATIONS

Official Action (with English translation) for Chinese Patent Application No. 201410045229.7 dated Aug. 20, 2015, 14 pages.
Official Action (with English translation) for Japanese Patent Application No. 2013-026351 mailed Nov. 17, 2015, 7 pages.

* cited by examiner

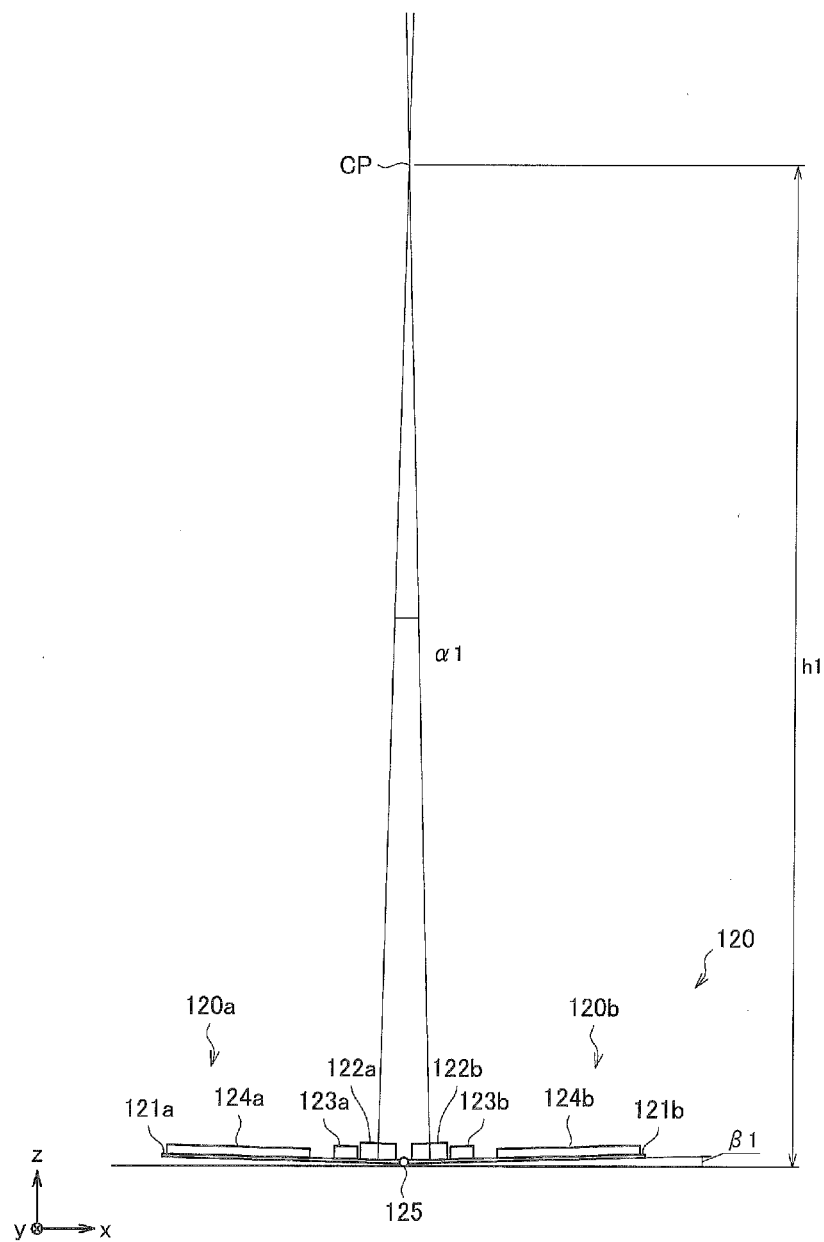

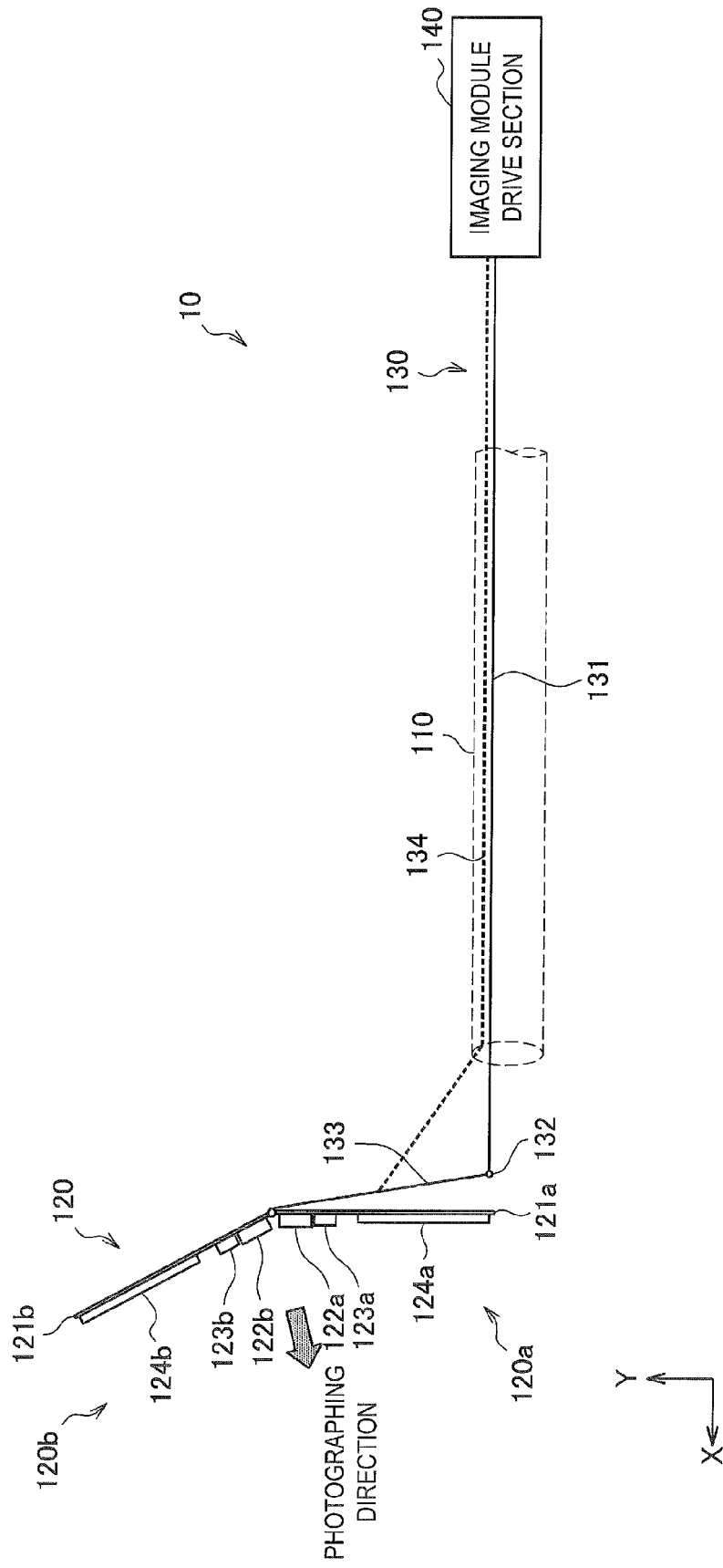

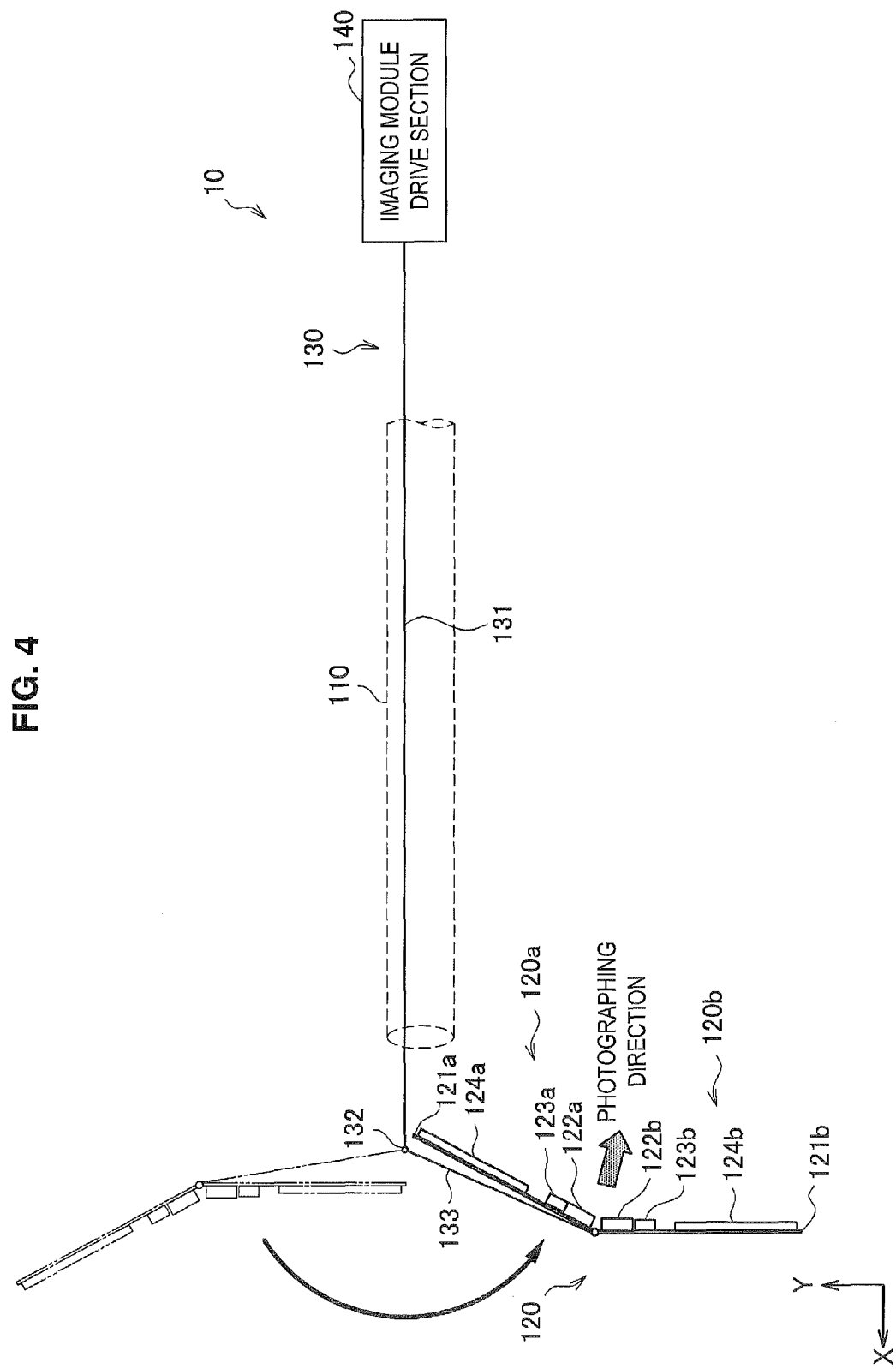

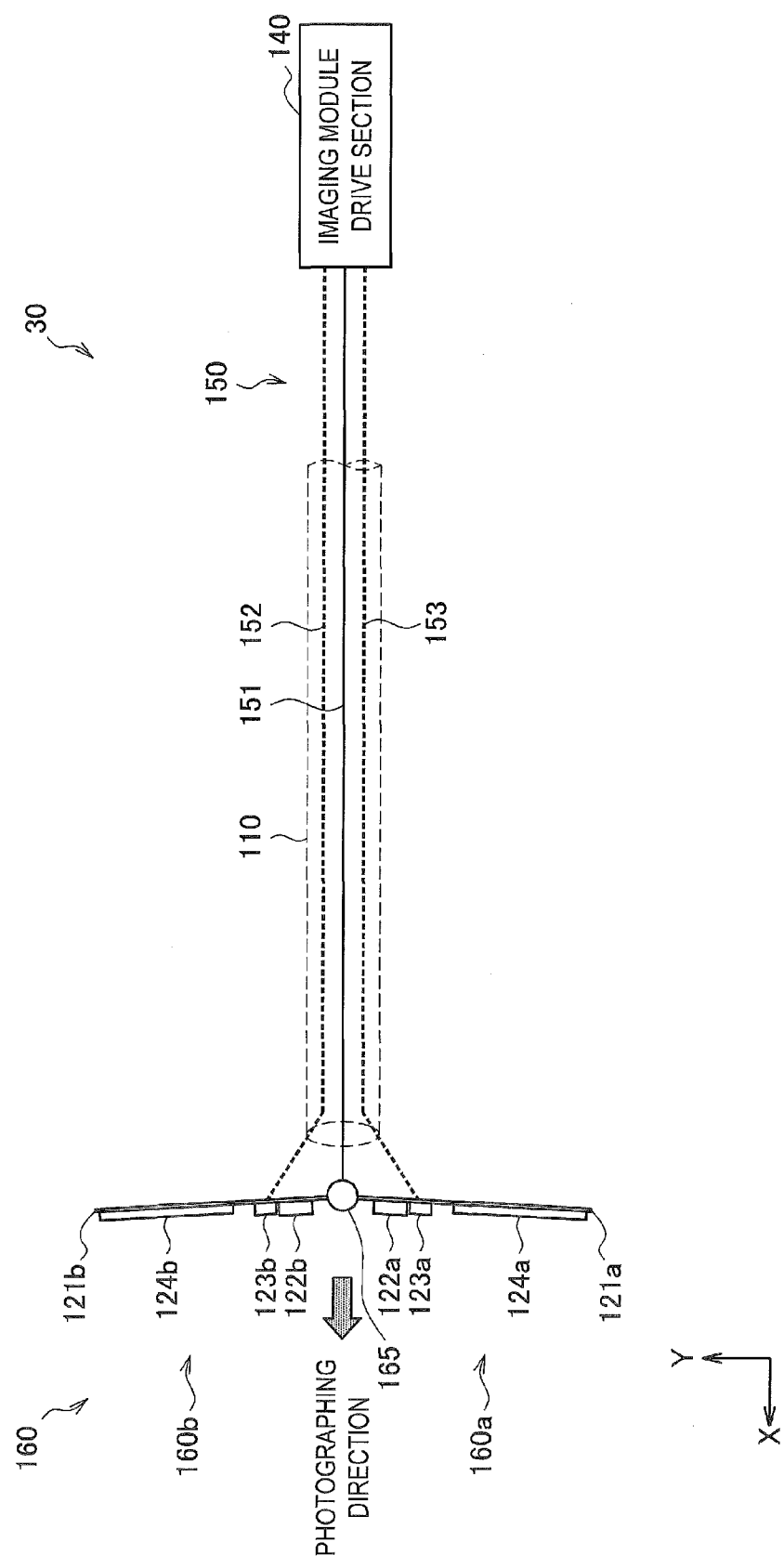

ENDOSCOPE APPARATUS WITH ROTATABLE IMAGING MODULE

CROSS REFERENCE TO RELATED APPLICATIONS

This application claims the benefit of Japanese Priority Patent Application JP 2013-026351 filed Feb. 14, 2013, the entire contents of which are incorporated herein by reference.

BACKGROUND

The present disclosure relates to an endoscope and an endoscope apparatus.

Observing (photographing) an affected part or performing various treatments for an affected part by using an endoscope has become widespread, from the viewpoint of minimally invasive medical treatment which reduces the physical burden on a patient (a person under measurement) as much as possible. In order to implement such minimally invasive medical treatment, a thickness (diameter) of a lens barrel of the endoscope inserted within the body cavity of a person under measurement is generally sought after which is equal to or less than approximately several mm.

On the other hand, three-dimensional endoscopes (3D endoscopes) which can display photographed positions as three-dimensional images (3D images) have become widespread in recent years. In 3D endoscopes, 3D images are generated based on pixel signals (image signals) acquired by each of a pair of image sensors included in the distal end of the lens barrel of the endoscope. Since various treatments can be performed by using a 3D endoscope while referring to 3D images close to what is actually seen by the human eyes, it becomes possible for a medical practitioner (a user) to operate the endoscope more intuitively.

Here, in a 3D endoscope, in order to secure a sufficient photographing range for treating an affected part, it is preferable that a prescribed distance is secured as an interval between the pair of image sensors. However, when the pair of image sensors is arranged while securing this prescribed distance in the distal end of the lens barrel of the endoscope, there is the possibility that the diameter of this lens barrel part will increase. Accordingly, technology has been developed in which the image sensors are stored within the lens barrel, while moving up to an affected part, inside the body cavity of the person under measurement, and photography is performed by allowing the image sensors to be projected from within the lens barrel at the time when the affected part is reached.

For example, JP S63-294508A discloses a stereoscopic endoscope apparatus which has a pair of imaging sections projecting in a radial direction of a lens barrel from mutually different positions of the outer surface of the lens barrel. Further, JP H4-500768A discloses an endoscope which has a pair of imaging sections included at mutually different positions on the outer wall of a lens barrel, which project in a radial direction of the lens barrel by eccentrically rotating with respect to the center of the end surface at the distal end of the lens barrel, around a rotation axis parallel to an extension direction of the lens barrel.

SUMMARY

On the other hand, in order to photograph higher quality images as 3D images in a 3D endoscope, the angle formed by the imaging surfaces of the pair of image sensors will become an important factor. Since changing the angle formed by the imaging surfaces corresponds to changing a so-called angle of convergence, when the angle formed by these imaging surfaces changes from a desired angle, a deviation may occur between a projection amount or depth amount in the 3D images (the amount of the image which can be seen by the user to project or recede) and the actual distance from the image sensors up to biological tissue which is a photographic subject, and this deviation may become an obstacle when a user performs intuitive operations. Here, the angle of convergence is an angle formed by straight lines extending in directions perpendicular to the imaging surfaces of the pair of image sensors (visual direction or optical axis direction).

Further, as described above, a photographing range photographed by a 3D endoscope influences the interval when setting the pair of image sensors. In this way, for a pair of image sensors in a 3D endoscope, the interval between the image sensors or the angle formed by the imaging surfaces will influence the quality of photographed 3D images.

Here, in the technology disclosed in JP S63-294508A and JP H4-500768A, the imaging sections which have image sensors are independently projected from mutually different positions of the lens barrel of the endoscope. Therefore, there is the possibility that a geometric arrangement relation, such as the interval between the image sensors or the angle formed by the imaging surfaces of the image sensors, deviates from a designed value originally obtained, due to mechanical distortions or the like. In addition, in the technology disclosed in JP H4-500768A, since the pair of image sensors project from mutually different positions with respect to an extension direction of the lens barrel, the distances from the image sensors up to a photographic subject will each be different. Therefore, in order to obtain high quality 3D images, a complex image signal process to correct this difference in distance or the like may be necessary, and there is the possibility that this will lead to an increase in cost.

By considering the above described situation, high quality 3D images have been sought after which are acquired more stably, without allowing the diameter of the lens barrel to increase. Accordingly, the present disclosure proposes a new and improved endoscope and endoscope apparatus capable of acquiring 3D images more stably.

According to an embodiment of the present disclosure, there is provided an endoscope including a lens barrel in which a partial region including at least a distal end is inserted inside a body cavity of a person under measurement, and an imaging module provided in the distal end of the lens barrel, the imaging module has at least one pair of image sensors arranged in parallel at a mutually prescribed distance. The imaging module is switched between a storage state in which the imaging module is stored within the lens barrel in a manner that an extension direction of imaging surfaces of the image sensors becomes a direction along a first direction which is an extension direction of the lens barrel, and a photographing state in which the imaging module is projected outside of the lens barrel in a manner that the extension direction of the imaging surfaces of the image sensors becomes a direction along a second direction which is a direction different from the first direction.

According to an embodiment of the present disclosure, there is provided an endoscope apparatus including an endoscope including a lens barrel in which a partial region including at least a distal end is inserted inside a body cavity of a person under measurement, and an imaging module provided in the distal end of the lens barrel, the imaging module including at least one pair of image sensors arranged in parallel at a mutually prescribed distance and being switched between a storage state in which the imaging module is stored within the lens barrel in a manner that an extension direction of imaging surfaces of the image sensors becomes a direction along a first direction which is an extension direction of the lens barrel, and a photographing state in which the imaging module is projected outside of the lens barrel in a manner that the extension direction of the imaging surfaces of the image sensors becomes a direction along a second direction which is a direction different from the first direction, and an imaging module drive control section which controls at least the switching between the storage state and the photographing state in the imaging module.

According to an embodiment of the present disclosure, the pair of image sensors may be integrally incorporated into the imaging module. Therefore, the distance between the pair of image sensors or the angle formed by the imaging surfaces of the pair of image sensors is fixed to a prescribed value more stably, and it becomes possible to acquire 3D images more stably.

According to the above described embodiments of the present disclosure, it becomes possible to acquire three-dimensional images more stably.

BRIEF DESCRIPTION OF THE DRAWINGS

FIG. 2B is a side view which shows a schematic configuration of the imaging module according to the first embodiment with a different cross point (CP) angle;

FIG. 3B is an explanatory diagram for describing a schematic configuration of the endoscope according to the first embodiment in a photographing state;

FIG. 4 is an explanatory diagram for describing a schematic configuration of the endoscope in a photographing state, according to a modified example of the first embodiment;

FIG. 5B is an explanatory diagram for describing a schematic configuration of the endoscope according the second embodiment in a photographing state.

DETAILED DESCRIPTION OF THE EMBODIMENT(S)

Figure 1:
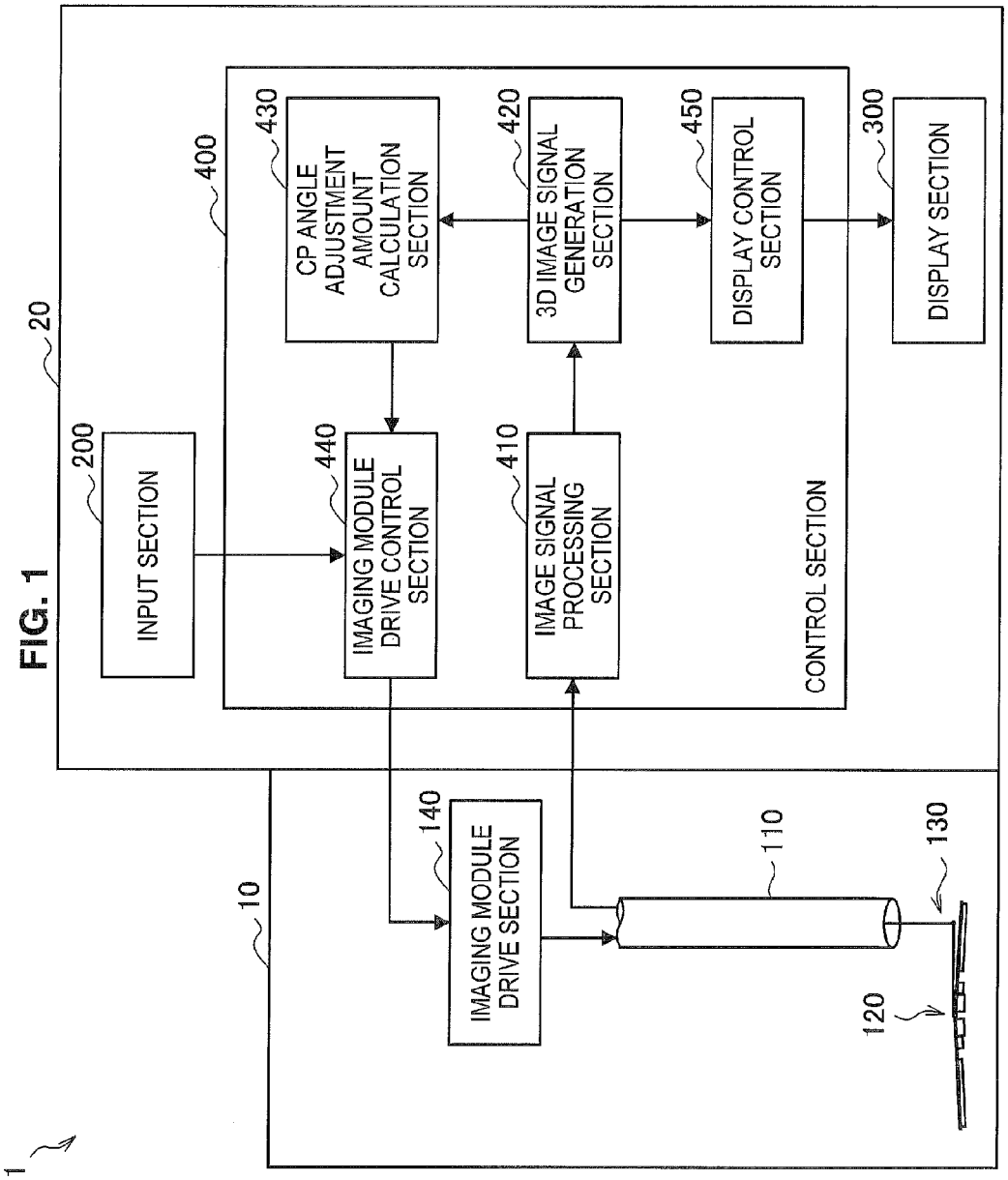
FIG. 1 is a schematic diagram which shows a configuration example of an endoscope apparatus according to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be given in the following order.
1. The first embodiment
  1-1. Configuration of the endoscope apparatus
  1-2. Configuration of the imaging module
  1-3. Configuration of the endoscope (storage state and photographing state)
2. The second embodiment
  2-1. Configuration of the endoscope (storage state and photographing state)
3. Conclusion 1. The First Embodiment

[1-1. Configuration of the Endoscope Apparatus]

First, a schematic configuration of an endoscope apparatus according to a first embodiment of the present disclosure will be described by referring to FIG. 1. FIG. 1 is a schematic diagram which shows a configuration example of the endoscope apparatus according to the first embodiment of the present disclosure.

With reference to FIG. 1, an endoscope apparatus 1 according to the first embodiment of the present disclosure includes an endoscope 10 and an apparatus body 20.

The endoscope 10 has functions which photograph the various biological tissues inside the body cavity of a patient (a person under measurement) and perform various treatments for an affected part. The endoscope 10 has a tubular shape, and a partial region including this distal end is inserted inside the body cavity of the person under measurement. An imaging section for photographing biological tissues of the person under measurement, a treatment tool for performing various treatments for an affected part, and a washing nozzle which spouts water or air for washing the lens of the imaging section or the like, can be included in this distal end of the endoscope 10. A medical practitioner (a user) operates the endoscope 10, allows this distal end to move up to an affected part inside the body cavity of the person under measurement, observes (photographs) desired biological tissues in this affected part, and can apply various treatments for this affected part. Note that, in the following description, the name for a series of processes for the person under measurement performed by the endoscope 10 will be called a "medical treatment". Therefore, in the following description, the various processes performed for the person under measurement by the endoscope 10, such as photographing an affected part (a region to be photographed) by a photographing function of the endoscope 10, and applying some treatment to the affected part by a treatment tool included in the endoscope 10, will be included in the "medical treatment".

Here, in the following description, from among the functions of the endoscope 10, the photographing function will mainly be described and a detailed description for the functions other than this, that is, for the treatment tool and the washing nozzle, will be omitted. Therefore, in the present embodiment, a configuration related to the photographing function in the endoscope 1 will mainly be illustrated, and configurations other than this will be omitted from that which is illustrated. Further, while a description will be made in the following description for a case where the endoscope 10 is a rigid endoscope (a hard mirror), the type of the endoscope 10 is not limited to the example in the present embodiment. For example, the endoscope 10 may be a flexible endoscope (a flexible mirror).

A configuration of the endoscope 10 will be described in detail by referring to FIG. 1. The endoscope 10 has a lens barrel 110, an imaging module 120, an imaging module connection section 130, and an imaging module drive section 140.

The lens barrel 110 has a tubular shape, and various mechanisms, such as the imaging module 120 (corresponding to the above described imaging section), a treatment tool, and a washing nozzle, are included in this distal end. These various mechanisms are electrically or mechanically connected to the apparatus body 20 by cables or wires extending inside the lens barrel 110, and are driven by a control from the apparatus body 20.

Further, the various mechanisms such as the imaging module 120 and the treatment tool are configured to be capable of being stored inside the lens barrel 110, and to be projected outside the lens barrel, as necessary. For example, at the stage when the lens barrel 110 is inserted inside the body cavity of a person under measurement, each mechanism is stored inside the lens barrel 110, and at the stage when this distal end reaches an affected part or a position to be observed, each mechanism is projected outside of the lens barrel 110, and various processes such as photography and treatment are performed. Note that, in the following description, a state in which each mechanism, and in particular, the imaging module 120, is stored inside the lens barrel 110 will be called a storage state, and a state in which each mechanism, and in particular, the imaging module 120, is projected outside the lens barrel 110 will be called a photographing state.

Further, while not clearly shown in FIG. 1, a joint section may be included at a prescribed position in an extension direction of the lens barrel 110, and it may be possible for the portion which includes the distal end of the lens barrel 110, and in particular, the portion inserted inside the body cavity of the person under measurement, to be replaced. That is, the portion of the endoscope 10 according to the present embodiment inserted inside the body cavity of the person under measurement may be a so-called disposable type. By setting the endoscope 10 as a disposable type, it becomes possible to perform more sanitary medical treatment, when compared to the case of repeatedly using the portion while performing maintenance such as washing or disinfecting. Further, since it may be unnecessary for maintenance such as washing or disinfecting to be performed after being used, the cost which may be necessary for this maintenance can be reduced. In addition, an advantage is also produced in which this type of endoscope can be used widely, even if the environment in which equipment for performing maintenance such as washing or disinfecting is not sufficiently widespread (for example, medical sites in developing countries or the like). However, the endoscope 10 according to the present embodiment is not limited to a disposable type, and may be repeatedly used by performing maintenance such as washing or disinfecting.

The imaging module 120 has image sensors and light sources, and has a function which photographs inside the body cavity of a person under measurement. In the present embodiment, the imaging module 120 has at least one pair of image sensors arranged in parallel at a prescribed distance, and can acquire image signals for generating three-dimensional images (3D images) with these image sensors. Further, the image sensors of the imaging module 120 may be arranged so that straight lines extending in directions perpendicular to the imaging surfaces are approximately parallel to each other, or may be arranged with an angle formed by the imaging surfaces having a prescribed angle, so that straight lines extending in directions perpendicular to the imaging surfaces intersect each other in a photographing direction (the direction in which the imaging surfaces are facing). Here, in the following description, the direction perpendicular to the imaging surfaces, in the at least one pair of image sensors of the imaging module 120, will be called an optical axis direction of the image sensors or a visual direction of the image sensors. In the case where the image sensors of the imaging module 120 are arranged so that straight lines extending in these optical axis directions become approximately parallel to each other, image signals for generating 3D images may be acquired using a so-called parallel method. Further, in the case where the image sensors of the imaging module 120 are arranged so that straight lines extending in these optical axis directions intersect each other in the photographing direction, image signals for generating 3D images may be acquired using a so-called intersection method. Note that, in the following description, the point at which straight lines extending in a direction perpendicular to the imaging surfaces intersect each other will be called a cross point (CP). Further, the angle formed by the imaging surfaces of the pair of image sensors of the imaging module 120 will be called a CP corner, and the angle of the CP corner will be called a CP angle. A configuration of the imaging module 120 will be described in detail later by referring to FIGS. 2A to 2D.

Note that, in the present embodiment, the photographing form of the imaging module 120 is not particularly limited, and may be any type of photographing form. For example, the imaging module 120 may photograph moving images, or may photograph still images. In the case where the imaging module 120 photographs moving images, the photographing timing may be a prescribed timing determined in advance, and may be controlled so as to perform photography at the prescribed timing by the apparatus body 20. In addition, the images photographed by the imaging module 120 may be color images, or may be monochrome images.

The imaging module connection section 130 is included inside the lens barrel 110, and electrically or mechanically connects the imaging module 120 and the apparatus body 20. Specifically, the imaging module connection section 130 has shafts, springs, wires, cables or the like, with one end connected to the imaging module 120, and the other end connected to the apparatus body 20 via the imaging module drive section 140. For example, the imaging module connection section 130 is connected to the imaging module 120 and the apparatus body 20 by a cable in a state capable of mutually transmitting and receiving signals, and signals related to the various controls relating to photographing conditions (various conditions related to photographing, such as the brightness of irradiated light from exposure or light sources, or the angle of the CP angle and the angle of convergence) are transmitted from the apparatus body 20 to the imaging module 120, and image signals are transmitted from the imaging module 120 to the apparatus body 20. Further, the imaging module connection section 130 is driven by the imaging module drive section 140 by a control from the apparatus body 20, and for example, can shift to a photographing state by pushing the imaging module 120 outside of the lens barrel 110, via a shaft or the like, and can shift to a storage state by drawing the imaging module 120 inside the lens barrel 110.

The imaging module drive section 140 controls the driving of the imaging module connection section 130, by a control from the apparatus body 20. Specifically, for example, the imaging module drive section 140 performs shifting between a storage state and a photographing state for the imaging module 120, by allowing the constituent members of the imaging module connection section 130 such as the shafts or springs to operate by prescribed conditions. Note that, switching between the storage state and the photographing state by the imaging module connection section 130 and the imaging module drive section 140 such as described above will be described in detail later by referring to FIG. 3A and FIG. 3B.

Next, a configuration of the apparatus body 20 will be described. The apparatus body 20 includes an input section 200, a display section 300, and a control section 400.

The input section 200 is an interface for inputting various types of information to the endoscope apparatus 1. The various types of information input from the input section 200 are input to the control section 400, and various processes are performed in accordance with this information by the control section 400. Specifically, for example, the input section 200 is an operation mechanism which is operated by a user, such as a mouse, keyboard, buttons, switches or levers. Further, for example, the input section 200 may be a remote control mechanism using infrared rays or other electric waves (a so-called remote control), or may be an external connection device such as a PDA. In addition, for example, the input section 200 is constituted of an input control circuit or the like, which generates input signals based on information input by the user who is using the above described operation mechanism, and outputs the generated input signals to the control section 400. By operating this input section 200, a user of the endoscope apparatus 1 can input various data to the endoscope apparatus 1 and can specify the process operations.

Specifically, for example, various operations may be controlled in the imaging module 120 of the endoscope 10, by having various commands (signals) input to the imaging module drive control section 440, which will be described later, from the input section 200. The operation of the imaging module 120 may shift between a photographing state and a storage state, and may perform changes of the photographing conditions or the like.

The display section 300 is an example of an output device, and is constituted by a device capable of displaying various types of information on a display screen, such as a monitor or a display, and notifies a user visually. For example, as such a device, there are display devices such as a CRT display device, a liquid crystal display device, a plasma display device, or an EL display device. The display section 300 displays, on this display screen, results obtained by the various processes performed by the endoscope apparatus 1 in a form such as text or images, by a control from the display control section 450, which will be described later. For example, the display section 300 can display, on this display screen, images inside the body cavity of a person under measurement photographed by the imaging module 120, as moving images in real time in three-dimensions. However, in the present embodiment, the images of inside the body cavity displayed by the display section 300 are not limited to such an example, and the display section 300 may display two-dimensional images, or may display still images.

The control section 400 controls the endoscope apparatus 1 in an integrated manner, and controls the various operations in the endoscope 10. Note that, since the functions other than the control of the photographing function in the endoscope 10 (for example, the functions which control operations such as the treatment tool and the washing nozzle), from among the functions of the control section 400, are the same as the functions for a control section of a known endoscope apparatus, a detailed description of these functions will be omitted, and here a description will mainly be made for the function related to the control of the photographing function.

The control section 400 has an image signal processing section 410, a 3D image signal generation section 420, a cross point (CP) angle adjustment amount calculation section 430, an imaging module drive control section 440, and a display control section 450.

The image signal processing section 410 receives, from the imaging module 120, signals (image signals) related to the images photographed by the image sensors of the imaging module 120, and applies various signal processes to these image signals. Here, the various signal processes may be processes which correct the noise component or luminance in the image signals, and includes, for example, a process which corrects pixel defects, a process which corrects an optical black level, a process which corrects shading characteristics, and a process which corrects luminance (a gamma correction process). However, the signal processes performed by the image signal processing section 410 are not limited to these processes, and any of the known signal processes in image processing technology may be performed as necessary. For example, the image signal processing section 410 may perform a filtering process which cuts the component of a specific wavelength for the image signals. Further, as described above, since the imaging module 120 in the present embodiment has at least one pair of image sensors, at least two types of image signals are input to the image signal processing section 410. The image signal processing section 410 can perform various image signal processes for each of these two types of image signals. The image signal processing section 410 transmits image signals, to which various signal processes are applied, to the 3D image signal generation section 420.

The 3D image signal generation section 420 generates image signals for 3D images, by using the image signals received from the image signal processing section 410. Here, in order to allow a user to recognize images inside the body cavity of the person under measurement as 3D images, based on the image signals acquired by the at least one pair of image sensors of the imaging module 120, there may be a so-called process in which image signals for the left eye and the right eye are generated with the signals for 3D images. Note that, in the present embodiment, the form in which the 3D images are displayed is not limited, and for example, a so called known display may be used, such as a glasses type or a naked-eye type. Further, in the present embodiment, the method in which the 3D images are displayed is not limited, and for example, at least one of a so-called parallel method and an intersection method may be selected in accordance with the configuration of the imaging module 120. In this way, various signal processes may be performed, in the 3D image signal generation section 420, which correspond to so-called known display forms and display methods of 3D images. The 3D image signal generation section 420 transmits the generated image signals for 3D images to the CP angle adjustment amount calculation section 430 and the display control section 450.

The CP angle adjustment amount calculation section 430 calculates an adjustment amount of the CP angle of the imaging module 120, in order for a distance from the imaging module 120 up to the CP to be adjusted, based on the transmitted image signals for 3D images. In the present embodiment, as will be described later by referring to FIG.

Figure 2A:
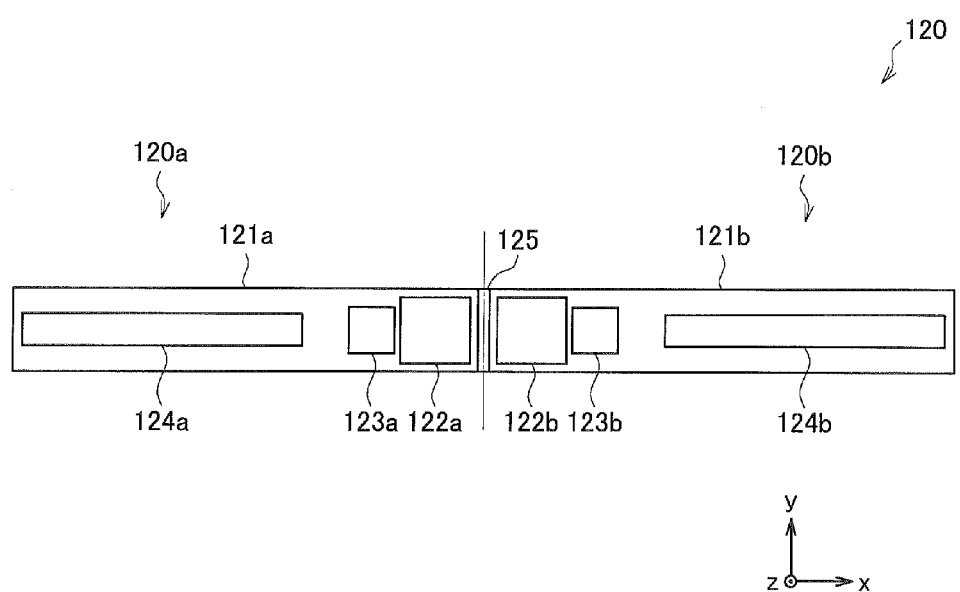
FIG. 2A is an upper view which shows a schematic configuration of an imaging module according to the first embodiment.
Figure 2C:
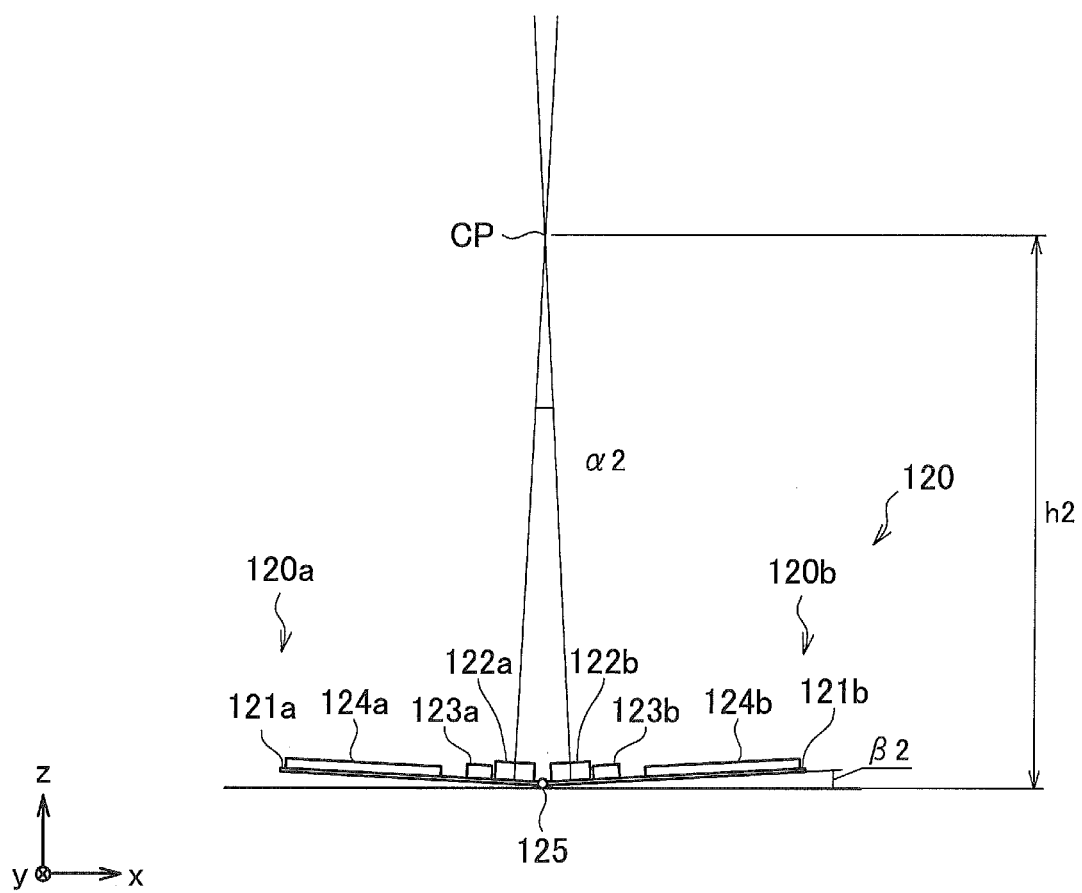
FIG. 2C is a side view which shows a schematic configuration of the imaging module according to the first embodiment with a different cross point (CP) angle.
Figure 2D:
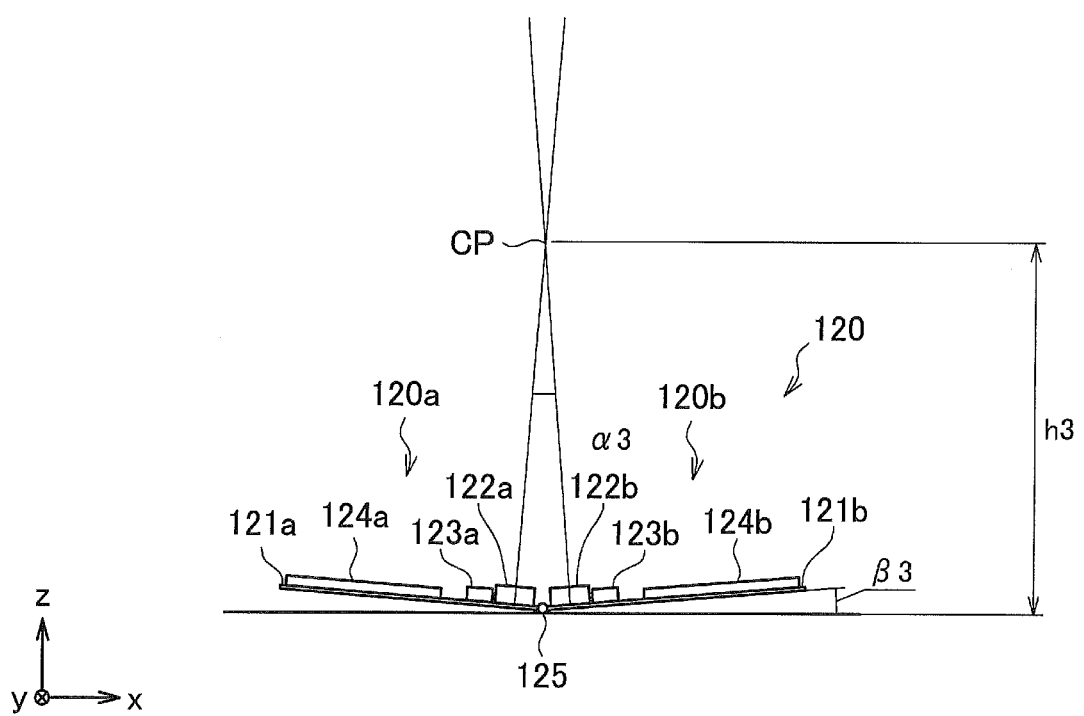
FIG. 2D is a side view which shows a schematic configuration of the imaging module according to the first embodiment with a different cross point (CP) angle.

2A to FIG. 2D, the distance from the imaging module 120 and the image sensors up to the CP may be adjusted, by allowing the CP angle to be adjusted in the imaging module 120. For example, the CP angle adjustment amount calculation section 430 can calculate an adjustment amount of the CP angle so that the CP is positioned in a region to be photographed inside the body cavity of a person under measurement. Here, in a 3D image, the distance from the imaging module 120 and the image sensors up to the CP is closely related to this projection amount or depth amount (the amount of the image which can be seen by the user to project or recede). Therefore, since a zero point of the projection amount or depth amount in a 3D image is adjusted near to a region to be photographed, for example, a position to be observed, by having the CP angle adjusted so that the CP is positioned in the region to be photographed, it becomes possible to perform treatments by more intuitive operations, when a user performs various treatments while referring to 3D images. The CP angle adjustment amount calculation section 430 transmits the calculated adjustment amount of the CP angle to the imaging module drive control section 440.

The imaging module drive control section 440 controls the driving of the various mechanisms in the imaging module 120 of the endoscope 10. For example, the imaging module drive control section 440 controls the driving of the image sensors of the imaging module 120, and can allow various conditions related to photographing, such as exposure or photographing timing, to be changed. Further, for example, the imaging module drive control section 440 controls the driving of the light sources of the imaging module 120, and can allow light to be irradiated at a prescribed timing from these light sources, and can allow the amount of light from these light sources to be adjusted. In addition, for example, the imaging module drive control section 440 can mechanically or electrically control the operations of the imaging module 120, by controlling the driving of the imaging module connection section 130, and can allow shifting between the storage state and the photographing state. Further, the imaging module drive control section 440 can allow the CP angle of the imaging module 120 to be changed, based on the adjustment amount of the CP angle calculated by the CP angle adjustment amount calculation section 430.

Here, as described above, the endoscope 10 may have mechanisms, other than a photographing function, such as a treatment tool for performing various treatments for an affected part, or a washing nozzle for washing the imaging module 120 or the like. Therefore, the endoscope apparatus 1 may additionally have an endoscope drive section which drives these mechanisms in the endoscope 10, or an endoscope drive control section which totally controls the driving of these mechanisms. That is, the endoscope 10 may additionally have an endoscope drive section which drives various types of known mechanisms of a general endoscope, which includes mechanisms such as various types of treatment tools or washing nozzles, for example, and the control section 400 may additionally have an endoscope drive control section for controlling the driving of the endoscope by this endoscope drive section.

Further, in the present embodiment, control of the driving of the endoscope 10 by the imaging module drive control section 440 and the endoscope drive control section may be automatically performed based on a program or the like input to the endoscope apparatus 1 in advance, or may be performed at an arbitrary timing by having control contents input to the imaging module drive control section 440 and the endoscope drive control section by a user via the input section 200. For example, the driving of the imaging module 120 by the imaging module drive control section 440 may be controlled, by a program, so that shifting between the storage state and the photographing state of the imaging module 120 automatically changes from the storage state during the time when the distal end of the endoscope 10 moves inside the body cavity of a patient, to the photographing state at the time when the distal end of the endoscope 10 reaches a region to be photographed inside the body cavity of a patient. Further, for example, the driving of the imaging module 120 by the imaging module drive control section 440 may be controlled so that switching between the storage state and the photographing state of the imaging module 120 is performed at an arbitrary timing, by an operation via the input section 200 by a user. In this way, instructions for the driving control of the endoscope 10 may be automatically provided to the imaging module drive control section 440 and the endoscope drive control section by a program or the like, so that the endoscope 10 performs the prescribed driving at a prescribed timing, or may be provided externally by a user so that the endoscope 10 performs arbitrary driving at an arbitrary timing. Therefore, in the present embodiment, the method which provides commands related to the driving control of the endoscope 10 to the imaging module drive control section 440 and the endoscope drive control section is not particularly limited, and may be arbitrary selected, by considering the convenience of the user or safety at the time of performing medical treatment.

The display control section 450 performs a control which displays various data on the display screen of the display section 300. For example, the display control section 450 allows various types of images photographed by the imaging module 120 to be displayed as moving images in real time on the display screen of the display section 300. Further, the display control section 450 may allow various types of information related to a person under measurement, which may be necessary when performing medical treatment (for example, body data such as height or weight, and personal data of the patient such as a history of previous medical treatments (a medical history)), to be displayed on the display screen of the display section 300. Note that, the images allowed to be displayed on the display screen of the display section 300 by the display control section 450 are not limited to 3D images, and may be two-dimensional images (2D images), or may be still images. Further, the display control section 450 may perform a control, such as allowing display by enlarging (zooming) a partial region of an image allowed to be displayed on the display screen of the display section 300, as necessary.

Here, while not clearly shown in FIG. 1, the endoscope apparatus 1 may additionally include each of the following constituent members.

For example, the endoscope apparatus 1 may additionally include a storage section which stores various data processed in the endoscope apparatus 1 and the processing results. For example, this storage section may be constituted by a magnetic storage device such as an HDD (Hard Disk Drive), a semiconductor storage device, an optical storage device, or a magneto-optical storage device, and these types of devices are not limited. This storage section can store programs or various data executed by the control section 400, or various data acquired from the outside. For example, this storage section may store images of inside the body cavity of a person under measurement, which have been photographed by the imaging module 120, as a history. Further, this storage section may store various types of information related to a person under measurement, which may be necessary in accordance with a medical treatment (for example, personal data of the patient). In addition, this storage section may store a log related to the various treatments performed for the person under measurement by using the endoscope apparatus 1. Further, such various types of information stored in this storage section may be displayed on the display screen of the display section 300 by the display control section 450, as necessary.

Further, for example, the endoscope apparatus 1 may additionally include a communication section which connects the endoscope apparatus 1 to other external apparatuses capable of mutual communication. A so-called known communication system can be used for the communication form of this communication section, regardless of whether it is wired or wireless. Further, this communication section may be connected to an arbitrary external apparatus via various communication networks, or may be connected directly to an arbitrary external apparatus. The endoscope apparatus 1 can transmit the various types of information stored in the above described storage section to this external apparatus, via this communication section. For example, in the case where various types of information related to a person under measurement are collectively managed in a storage apparatus such as a data server within a hospital, the endoscope apparatus 1 may transmit information related to a medical treatment result, such as observation results or treatment results of an affected part for the person under measurement, to this data server via this communication section, and may receive various types of information related to the person under measurement from this data server prior to performing a medical treatment.

Further, for example, the endoscope apparatus 1 may additionally include a display device such as a lamp, or a voice output device such as a speaker. For example, in the case where a problem occurs in the operation of the endoscope apparatus 1, a user may be notified of this fact, by allowing this lamp to be lit or by issuing a warning sound such as a buzzer or alarm from the speaker.

Heretofore, an example of the functions of the endoscope apparatus 1 according to the present embodiment, and in particular, an example of the functions of the control section 400, has been shown in detail by referring to FIG. 1. Note that, each of the constituent elements of the endoscope apparatus 1 may be constituted by using generic members or circuits, or may be constituted by hardware specializing in the functions of each of the constituent elements. Further, a CPU (Central Processing Unit) or the like may control all of the functions of each constituent element of the control section 400. Therefore, it is possible to arbitrarily change the configuration to be used, in accordance with the technology level at the time when implementing the present embodiment.

Further, it is possible to create a computer program for realizing each of the functions of the endoscope apparatus 1 and/or the control section 400 according to the present embodiment such as described above, and to implement the computer program in a personal computer or the like. Further, a recording medium can be provided capable of being read by a computer which stores such a computer program. For example, the recording medium is a magnetic disk, an optical disk, a magneto-optical, a flash memory or the like. Further, the above described computer program may be distributed via a network, without using a recording medium, for example.

[1-2. Configuration of the Imaging Module]

Next, a configuration of the imaging module 120 shown in FIG. 1 will be described in detail by referring to FIG. 2A to FIG. 2D. FIG. 2A is an upper view which shows a schematic configuration of the imaging module 120 according to the first embodiment. FIG. 2B to FIG. 2D are side views which show schematic configurations of the imaging module 120 according to the first embodiment with different cross point (CP) angles.

First, with reference to FIG. 2A, the imaging module 120 is constituted by combining a first imaging section 120a and a second imaging section 120b with a connection section 125. The first imaging section 120a has a first substrate 121a, a first image sensor 122a, a first light source 123a, and a first cable connector part 124a. Further, the second imaging section 120b has a second substrate 121b, a second image sensor 122b, a second light source 123b, and a second cable connector part 124b. Also, the first imaging section 120a and the second imaging section 120b are connected in the imaging module 120 so as to symmetrically sandwich the connection section 125. In this way, by having a pair of imaging sections (the first imaging section 120a and the second imaging section 120b) symmetrically arranged in the imaging module 120, 3D images can be generated by using so-called image signals for the left eye and right eye, which are acquired by each of the imaging sections.

In the first imaging section 120a, the first substrate 121a has an approximately rectangular shape, and the first image sensor 122a, the first light source 123a and the first cable connector part 124a are arranged on one of the surfaces so as to be aligned in one row in a direction along the long side of the first substrate 121a. Also, the short side nearest the first image sensor 122a, which is one of the short sides of the first substrate 121a, is connected to one of the short sides of the second substrate 121b, via the connection section 125. Also, in the second imaging section 120b, the second image sensor 122b, the second light source 123b and the second cable connector 124b are arranged on the second substrate 121b, on the surface of the same side as that of the first substrate 121a, so as to be symmetrically arranged with each element of the first imaging section 120a sandwiching the connection section 125. Note that, in the following description, the side on which each of the elements is arranged, in the first substrate 121a and the second substrate 121b, will be called an upper side or a surface side of the imaging module 120. Further, the opposite side to this surface side will be called a rear side of the imaging module 120. Further, in this way, since the first imaging section 120a and the second imaging section 120b have a symmetrical configuration in the imaging module 120, each constituent member of the first imaging section 120a will mainly be described in the following description, and a detailed description will be omitted for the second imaging section 120b.

The first image sensor 122a has an imaging surface on which light receiving elements are arranged in a two-dimensional shape, and light incident to this imaging surface is converted into electrical signals corresponding to this amount of light. By sequentially reading these electrical signals for each of the pixels constituted by one or a plurality of the light receiving elements, image signals corresponding to incident light is obtained. Note that, the timing at which each light receiving element is reset in the first image sensor 122a (the carriers accumulated within the light receiving elements are emptied), and the timing at which the image signals are read for each pixel, that is, the timing of opening and closing an electronic shutter (photographing timing), may be arbitrary controlled by the imaging module drive control section 440, in accordance with the photographing conditions. For example, the imaging module drive control section 440 may control the photographing timing, the exposure or the like in accordance with the brightness or the like around the imaging module 120, which changes in accordance with a drive condition of the first light source 123*a*. Further, for example, if there are cases where a moving image or a through image is photographed, the imaging module drive control section 440 may continuously read image signals from the first image sensor 122*a* at a prescribed photographing timing.

Note that, the type of the first image sensor 122*a* is not particularly limited in the present embodiment, and a so-called known image sensor may be used. For example, the first image sensor 122*a* may by a CMOS sensor, or may be a CCD sensor. However, in the present embodiment, it is preferable that an image sensor with a higher sensitivity is used for the first image sensor 122*a*, which is represented by a rear surface illumination type sensor, for example. This is because, since the inside of the body cavity of a human is generally dark, it is preferable to use an image sensor having a higher sensitivity in order to photograph clearer images.

The first light source 123*a* irradiates light to a region to be photographed, at the time when photographing in the imaging module 120. In the first light source 123*a*, this driving is controlled by the imaging module drive control section 440, and the timing which irradiates light, or this light amount, is controlled. For example, the imaging module drive control section 440 may arbitrarily adjust the amount of light from the first light source 123*a*, by considering the brightness or the like of an image photographed by the first image sensor 122*a*, in accordance with the photographed position. Further, for example, the imaging module drive control section 440 may control the timing at which the first light source 123*a* emits light, in accordance with the photographing timing of the first image sensor 122*a*.

Specifically, the first light source 123*a* may be an LED. In the case where the first light source 123*a* is an LED, the imaging module drive control section 440 can control this amount of light, the timing at which light is emitted or the like by adjusting a current amount applied to this LED. Further, this LED may be a white LED, for example. However, the light irradiated by the first light source 123*a* is not limited to white, and light of a specific wavelength bandwidth may be used, in accordance with this purpose of photographing. For example, the light irradiated by the first light source 123*a* may be near infrared light of a wavelength of 700 nm to 900 nm. In the case where the first light source 123*a* irradiates near infrared light, observation of an affected part using a florescent sign marker, such as an ICG (Indocyanine Green) solution, for example, may be performed. Note that, in the case where the first image sensor 122*a* irradiates near infrared light, image sensors which have imaging characteristics with a high spectral sensitivity for the wavelengths corresponding to near infrared light, for example, can be used as the first image sensor 122*a*. Further, the first light source 123*a* and the second light source 123*b* of the imaging module 120 may be constituted so as to irradiate light of wavelength bandwidths which are mutually different from each other, or may be constituted, for example, so that one of the light sources irradiates white light, and the other light source irradiates near infrared light. In the case where the first light source 123*a* and the second light source 123*b* irradiate light of mutually different wavelength bandwidths, the wavelength of light irradiated to a region to be photographed may be switched in accordance with the purpose of photographing, by a control of the imaging module drive control section 440.

The first cable connector part 124*a* is an interface for electrically connecting the imaging module 120 to the imaging module drive section 140 or the apparatus body 20. The first image sensor 122*a* and the first light source 123*a* are electrically connected to the cable connector part 124*a* by a cable or the like (not shown in the figures), and the first cable connector part 124*a* is connected to the imaging module drive section 140 or the apparatus body 20, by another additional cable or the like (not shown in the figures) extending inside the lens barrel 110. That is, the first image sensor 122*a* and the first light source 123*a* are electrically connected to the imaging module drive section 140 or the apparatus body 20, via the first cable connector part 124*a*, and can mutually exchange various types of information. For example, this driving is performed by having the first image sensor 122*a* and the first light source 123*a* connected to the imaging module drive section 140 via the first cable connector part 124*a*. Further, for example, the first image sensor 122*a* is connected to the image signal processing section 410 of the apparatus body 20, via the first cable connector part 124*a*, and can transmit the acquired image signals to the image signal processing section 410. Note that, for example, a method which directly attaches a cable, such as a pressure contact, can be used for a connection method of the first cable connector part 124*a* with various types of cables. Since another configuration may not be necessary for connecting the cables, by directly attaching the cables to the first cable connector part 124*a*, the volume occupied by the first cable connector part 124*a* can be reduced, and it becomes possible to make the imaging module 120 smaller.

Heretofore, a configuration of the first imaging section 120*a* has been described by referring to FIG. 2A. As described above, in the imaging module 120, the first imaging section 120*a* and the second imaging section 120*b*, which has a configuration similar to that of the first imaging section 120*a*, are symmetrically arranged by sandwiching the connection section 125. Therefore, as shown in FIG. 2A, in the present embodiment, the first cable connector part 124*a*, the first light source 123*a*, the first image sensor 122*a*, the second image sensor 122*b*, the second light source 123*b*, and the second cable connector part 124*b* are arranged, in this order, in one row on the first substrate 121*a* and the second substrate 121*b*. Here, in the following description, the direction of a straight line connecting the centers of the imaging surfaces of the first image sensor 122*a* and the second image sensor 122*b* will be defined as an X axis. That is, in FIG. 2A, the X axis is the long side direction of the first substrate 121*a* and the second substrate 121*b*. Further, the direction mutually perpendicular to the X axis, in a direction parallel to the imaging surfaces of the first image sensor 122*a* and the second image sensor 122*b*, will be defined as a Y axis. That is, in FIG. 2A, the Y axis is the short side direction (a depth direction of the surface in the figure) of the first substrate 121*a* and the second substrate 121*b*. In addition, the direction mutually perpendicular to the X axis and the Y axis will be defined as a Z axis. That is, in FIG. 2A, the Z axis is the direction perpendicular to the imaging surfaces of the first image sensor 122*a* and the second image sensor 122*b* (the visual direction or optical axis direction of the first image sensor 122*a* and the second image sensor 122*b*). Further, in FIG. 2A, the direction in which the imaging surfaces of the first image sensor 122*a* and the second image sensor 122*b* face each other will be defined as a positive direction of the Z axis. The positive direction of the Z axis corresponds to the photographing direction in the imaging module 120.

Here, in the example shown in FIG. 2A, while a case has been described in which the first image sensor 122*a* and the second image sensor 122*b* are arranged in the imaging module 120 so that an angle (that is, the CP angle) formed by the imaging surface of the first image sensor 122*a* and the imaging surface of the second image sensor 122*b* becomes approximately 180 degrees, the imaging surface of the first image sensor 122*a* and the second image sensor 122*b* are arranged, in the present embodiment, so as to have a prescribed CP angle less than 180 degrees. In the case where the CP angle is 180 degrees, 3D images are displayed using a so-called parallel method, based on the image signals acquired by the first imaging section 120*a* and the second imaging section 120*b*. On the other hand, in the case where the CP angle is less than 180 degrees, 3D images are displayed using a so-called intersection method, based on the image signals acquired by the first imaging section 120*a* and the second imaging section 120*b*. In the present embodiment, while a 3D image display process may be performed by any method, it is preferable that an intersection method is used, in which the processing amount of image signals is in general comparatively smaller in accordance with the generation process of 3D image signals. This is because, if the signal processing amount is small in accordance with the generation process of 3D image signals, a quicker response can be made up to when the image signals acquired by the imaging module 120 are displayed on the display section 300. When the imaging module 120 photographs a region to be photographed, and thereafter the latency up to when this image is displayed on the display section 300 is large, intuitive operations may become difficult for a user who performs the operations of the endoscope 10 while referring to the images displayed on the display section 300. Therefore, in the present embodiment, it is preferable that an intersection method is used from the viewpoint of reducing this latency as much as possible. Hereinafter, configurations of the imaging module 120 with CP angles less than 180 degrees will be described by referring to FIG. 2B to FIG. 2D.

FIG. 2B shows an example of the imaging module 120 which has a CP angle less than 180 degrees, and this CP angle is 177 degrees. That is, the first imaging section 120*a* and the second imaging section 120*b* are connected by the connection section 125, so that an angle $\beta 1$ formed by the first substrate 121*a* and the second substrate 121*b* with the X axis becomes 1.5 degrees.

Here, as shown in FIG. 2B, the point at which straight lines extending in the optical axis directions of the first image sensor 122*a* and the second image sensor 122*b* intersect each other is a CP. Further, an angle $\alpha 1$ formed by the straight lines extending in the optical axis directions of the first image sensor 122*a* and the second image sensor 122*b* is an angle of convergence in the CP. Further, in the following description, for example, a distance from the connection section 125 up to the CP, positioned in the center of the imaging module 120, will be called a CP distance. Note that, in FIG. 2B to FIG. 2D, the Z axis direction is the direction of this CP distance.

Here, by adjusting the CP distance, a zero point of the projection amount or depth amount in 3D images photographed by the imaging module 120 can be adjusted. For example, by performing photography with photography conditions such as the CP being positioned in a region to be photographed, that is, such as a distance from the imaging module 120 up to a region to be photographed becoming the CP distance, 3D images can be obtained in which the location at which this CP is positioned is set as a zero point. The CP distance is geometrically determined by an arrangement interval between the CP angle (that is, an angle formed by the imaging surface of the first image sensor 122*a* and the imaging surface of the second image sensor 122*b*) and the first image sensor 122*a* and the second image sensor 122*b*. That is, an arrangement position of the first image sensor 122*a* and the second image sensor 122*b* in the imaging module 120 may be determined, so as to have a desired CP distance. In the example shown in FIG. 2B, an arrangement position of the first image sensor 122*a* and the second image sensor 122*b* in the imaging module 120 is adjusted, so that a CP distance h1 becomes approximately 152 mm.

FIG. 2C shows an example of the imaging module 120 which has a CP angle less than 180 degrees, and this CP angle is 174 degrees and the angle of convergence is $\alpha 2$. That is, the first imaging section 120*a* and the second imaging section 120*b* are connected by the connection section 125, so that an angle $\beta 2$ formed by the first substrate 121*a* and the second substrate 121*b* with the X axis becomes 3.0 degrees. In the example shown in FIG. 2C, an arrangement position of the first image sensor 122*a* and the second image sensor 122*b* in the imaging module 120 is adjusted, so that a CP distance h2 becomes approximately 76.3 mm.

FIG. 2D shows an example of the imaging module 120 which has a CP angle less than 180 degrees, and this CP angle is 171 degrees and the angle of convergence is $\alpha 3$. That is, the first imaging section 120*a* and the second imaging section 120*b* are connected by the connection section 125, so that an angle $\beta 3$ formed by the first substrate 121*a* and the second substrate 121*b* with the X axis becomes 4.5 degrees. In the example shown in FIG. 2D, an arrangement position of the first image sensor 122*a* and the second image sensor 122*b* in the imaging module 120 is adjusted, so that a CP distance h3 becomes approximately 50.8 mm.

Heretofore, a configuration of the imaging module 120 according to the first embodiment has been described in detail by referring to FIG. 2A to FIG. 2D. Note that, while configurations of the imaging module 120 with the 4 types of CP angles shown in FIG. 2A to FIG. 2D have been described here as examples of the configurations of the imaging module 120 according to the first embodiment, the imaging module 120 according to the present embodiment is not limited to such examples, and may have a configuration which has another CP angle. Further, the CP angle of the imaging module 120 may be fixed to a prescribed value, or a function which changes the CP angle may be included in the imaging module 120, and the CP angle may be changed.

In the case where the CP angle is fixed to a prescribed value, a plurality of imaging modules 120 with mutually different CP angles are prepared in advance as the imaging modules 120, such as shown in FIG. 2B to FIG. 2D, for example, and it is possible to replace this plurality of imaging modules 120 in the distal end of the endoscope 10. Also, from the viewpoint in which the CP is positioned close to a region to be photographed in the imaging module 120, this plurality of imaging modules 120 may be used differently in accordance with the position of an affected part. For example, in the case where an affected part exists at a comparatively narrow position inside the body cavity, since it is assumed that photographing will be performed with a condition in which the distance between the imaging module 120 and a region to be photographed is comparatively short, an imaging module 120 may be used in which the CP angle is smaller and the CP distance is shorter. Further, for example, in the case where an affected part exists at a comparatively wide position inside the body cavity, since it is assumed that photographing will be performed with a condition in which the distance between the imaging module 120 and a region to be photographed is comparatively long, an imaging module 120 may be used in which the CP angle is larger and the CP distance is longer.

On the other hand, in the case where the CP angle is changeable, a drive mechanism, such as a motor or an actuator, is included in the connection section 125, for example, and by this drive mechanism, the first substrate 121a and the second substrate 121b may be capable of being mutually rotated, by setting the Y axis direction as a rotation axis direction around the connection section 125. That is, the imaging module 120 has a rotation mechanism, between the first image sensor 122a and the second image sensor 122b, which sets a direction parallel to the imaging surfaces of the first image sensor 122a and the second image sensor 122b as a rotation axis direction, in a direction perpendicular to the arrangement direction of the first image sensor 122a and the second image sensor 122b, the first image sensor 122a and the second image sensor 122b are capable of being mutually rotated by this rotation mechanism, and the CP angle may be adjusted by this rotation mechanism.

Further, in the case where the CP angle is changeable, driving of the rotation mechanism in the connection section 125 for adjusting such a CP angle may be controlled by the imaging module drive control section 440 of the apparatus body 20. That is, the imaging module drive control section 440 may adjust the CP angle of the imaging module 120, by allowing the rotation mechanism in the connection section 125 to be driven.

Specifically, as described above in "1-1. Configuration of the endoscope apparatus", first, when image signals are acquired by the first image sensor 122a and the second image sensor 122b of the imaging module 120, the image signal processing section 410 applies various signal processes to these image signals. Further, signals for 3D images are generated from these image signals, by the 3D image signal generation section 420, and 3D images of an affected part photographed by the display control section 450 are displayed on the display section 300. Here, there is the possibility that the projection amount or the depth amount in the 3D images displayed on the display section 300 will not be appropriate. Accordingly, since the CP distance is adjusted in the imaging module 120 by the CP angle adjustment amount calculation section 430, based on the generated signals for 3D images, an adjustment amount of the CP angle of the imaging module 120 is calculated. Specifically, an adjustment amount of the CP angle is calculated for positioning the CP at an affected part (a region to be photographed), by the CP angle adjustment amount calculation section 430. Information related to this calculated adjustment amount is transmitted to the imaging module drive control section 440, and the imaging module drive control section 440 adjusts the CP angle of the imaging module 120, by allowing the rotation mechanism in the connection section 125 of the imaging module 120 be driven, based on this adjustment amount. In this way, by having the CP angle of the imaging module 120 adjusted so that the CP is positioned in an affected part (a region to be photographed), a zero point of the projection amount or the depth amount in the 3D images is adjusted near to the affected part, and 3D images closer to what is seen by the human eyes are displayed on the display section 300.

[1-3. Configuration of the Endoscope (Storage State and Photographing State)]

Figure 3A:
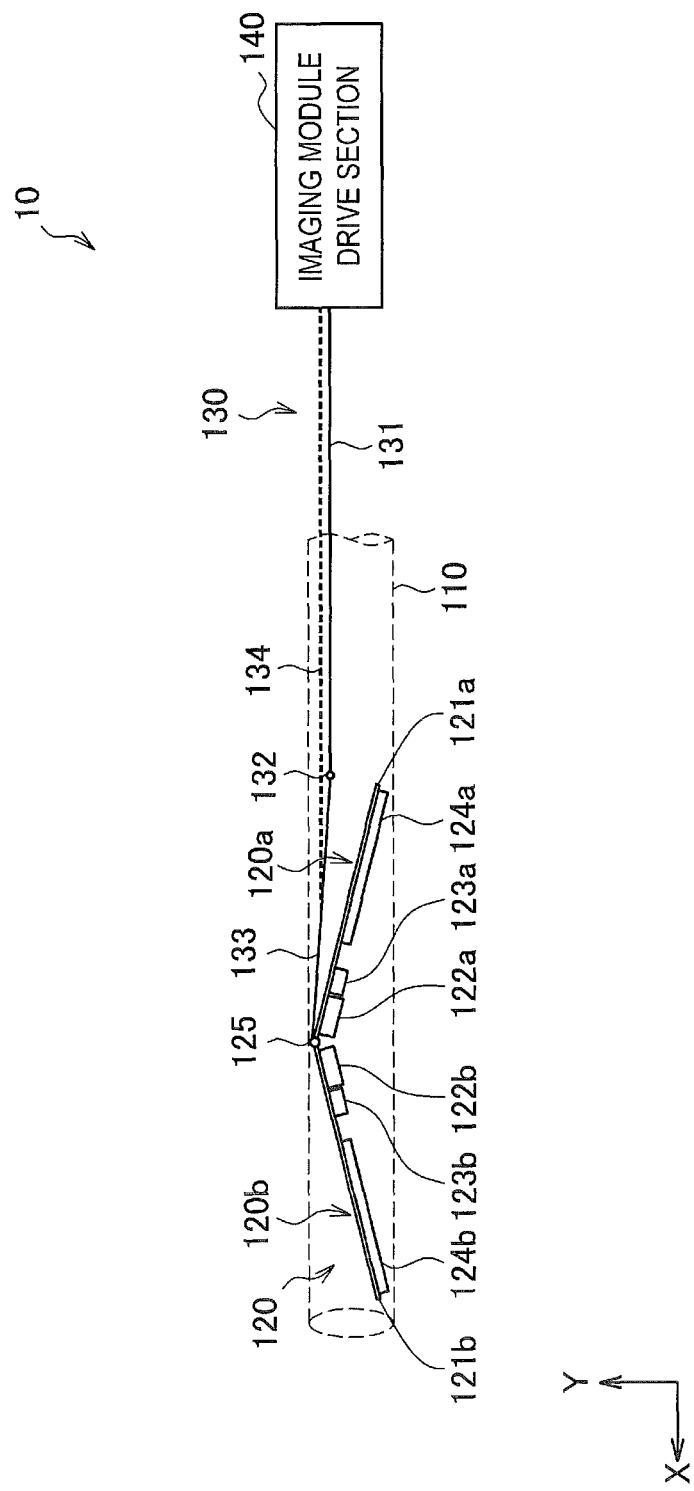
FIG. 3A is an explanatory diagram for describing a schematic configuration of an endoscope according to the first embodiment in a storage state.

Next, a configuration of the endoscope 10 according to the first embodiment, in a storage state and a photographing state, will be described in detail by referring to FIG. 3A and FIG. 3B. As described above in "1-1. Configuration of the endoscope apparatus", in the first embodiment, the endoscope 10 is switched between a storage state in which the imaging module 120 is stored within the lens barrel 110, and a photographing state in which the imaging module 120 is projected from the lens barrel 110. Specifically, for example, the endoscope 10 is in a storage state during the time when the distal end of the lens barrel 110 moves up to an affected part inside the body cavity of a person under measurement, and shifts to a photographing state at the time when the distal end of the lens barrel 110 reaches the affected part, and photographing of the affected part is performed. Hereinafter, a configuration of the endoscope 10 according to the first embodiment, in such a storage state and photographing state, will be described by referring to FIG. 3A and FIG. 3B. Note that, for simplicity, only the endoscope 10, that is, the lens barrel 110, the imaging module 120, the imaging module connection section 130 and the imaging module drive section 140, from among the endoscope apparatus 1 shown in FIG. 1, will be illustrated in FIG. 3A and FIG. 3B, and the constituent members other than these will be omitted in the illustration. Further, for simplicity, only the configuration of the lens barrel 110 and the imaging module connection section 130 near to this distal end will be illustrated in FIG. 3A and FIG. 3B. In addition, in order to describe the configuration of the imaging module 120 and the imaging module connection section 130 within the lens barrel 110, the outline of the lens barrel will be illustrated with only a dotted line. Here, FIG. 3A and FIG. 3B schematically show a configuration of the endoscope 10 in a storage state and in a photographing state, and the dimensions or the like of each constituent member is not limited to the example shown in FIG. 3A and FIG. 3B. Further, in FIG. 3A and FIG. 3B, the extension direction of the lens barrel 110 is defined as an X axis, and additionally, the distal end direction of the lens barrel 110 is defined as a positive direction of the X axis.

First, the endoscope 10 according to the first embodiment in a storage state will be described by referring to FIG. 3A. FIG. 3A is an explanatory diagram for describing a schematic configuration of the endoscope 10 according to the first embodiment in a storage state.

With reference to FIG. 3A, in the first embodiment, the imaging module 120 is stored within the lens barrel 110, in a storage state, so that an extension direction of the imaging surfaces of the first image sensor 122a and the second image sensor 122b becomes an extension direction of the lens barrel 110. Specifically, as shown in FIG. 3A, the imaging module 120 may be stored within the lens barrel 110, so that an arrangement direction of the first image sensor 122a and the second image sensor 122b becomes a direction along the extension direction of the lens barrel 110.

Further, the imaging module 120 is connected to the imaging module drive section 140, via the imaging module connection section 130 extending along the extension direction of the lens barrel 110 within the lens barrel 110. Here, the imaging module connection section 130 has a first shaft 131, a joint section 132, a second shaft 133, and an elastic member 134.

One end of the first shaft 131 is connected to the imaging module drive section 140, and this driving is controlled by the imaging module drive section 140. Specifically, for example, the imaging module drive section 140 can allow the first shaft 131 to move in the X axis direction, by applying a force to the first shaft 131 in the positive direction or the negative direction of the X axis. Further, the other end of the first shaft 131 is connected to one end of the second shaft 133 via the joint section 132.

The joint section 132 is a joint mechanism which has a rotation axis, and rotatably connects the first shaft 131 and the second shaft 133 to each other. Further, the end of the second shaft 133 on the opposite side to the side connected to the joint section 132 is connected to the imaging module 120. For example, one end of the second shaft 133 is connected near to the connection section 125 on the rear side of the imaging module 120. However, the position at which the second shaft 133 is connected to the imaging module 120 is not limited to such an example, and this connection position is not limited if there are positions at which shifting is performed smoothly between the storage state and the photographing state.

Further, the elastic member 134 extends between the imaging module drive section 140 and the second shaft 133, so as to extend along the first shaft 131 and the second shaft 133. Note that, the type of the elastic member 134 is not particularly limited, and elastic bodies of any type may be used. In the present embodiment, for example, the elastic member 134 is a tension spring. Here, the joint section 132 is set as a rotation axis, and the elastic member 134 applies a tension to the second shaft 133 in a direction angled approximately 90 degrees with respect to the first shaft 131. That is, the elastic member 134 applies a tension to the second shaft 133, so that the second shaft 133 is allowed to extend in a direction approximately orthogonal to an extension direction of the lens barrel 110. For example, in the example shown in FIG. 3A, a tension force is applied to the second shaft 133 by the elastic member 134, in a direction in which the second shaft 133 is angled with respect to the first shaft 131, that is, in the upper direction within the figure, so that the photographing direction of the imaging module 120 is facing the X axis direction. However, as shown in FIG. 3A, by having the imaging module 120 hook onto the inner wall of the lens barrel 110, in the storage state, movement in which the second shaft 133 is allowed to rotate with respect to the first shaft 131 is restrained by the elastic member 134. Here, in the following description of FIG. 3A and FIG. 3B, the direction in which the elastic member 134 allows the second shaft 133 to extend (the vertical direction within the figure) is defined as a Y axis.

Next, the endoscope 10 according to the first embodiment in a photographing state will be described by referring to FIG. 3B. FIG. 3B is an explanatory diagram for describing a schematic configuration of the endoscope 10 according to the first embodiment in a photographing state. However, FIG. 3B schematically shows a configuration of the endoscope 10, and does not mean that the dimensions or the like of each constituent member are limited to the example shown in FIG. 3B.

With reference to FIG. 3B, in the first embodiment, the imaging module 120 is projected outside of the lens barrel 110, in a photographing state, so that an extension direction of the imaging surfaces of the first image sensor 122a and the second image sensor 122b becomes a direction along a direction different from the extension direction of the lens barrel 110. Specifically, as shown in FIG. 3B, the imaging module 120 may project from the lens barrel 110, so that an arrangement direction of the first image sensor 122a and the second image sensor 122b becomes a direction along a direction approximately orthogonal to the extension direction of the lens barrel 110 (the Y axis direction).

In the case of shifting from the storage state to the photographing state, in the storage state shown in FIG. 3A, the imaging module connection section 130 and the imaging module 120 are pushed out from within the lens barrel 110 in the positive direction of the X axis, by the imaging module drive section 140. Since the restraint of the force which allows the second shaft 133 to rotate by the elastic member 134 will disappear when the imaging module 120 is completely projected outside from the lens barrel 110, the second shaft 133 is angled in a direction approximately 90 degrees with respect to the first shaft 131 (the Y axis direction) around the joint section 132, and shifts to the photographing state.

Here, in the present embodiment, a direction in which the elastic member 134 is allowed to rotate the second shaft 133 may be any direction if a direction different from the extension direction of the lens barrel 110, and is not limited to the example shown in FIG. 3B. However, in the present embodiment, the extension direction of the second shaft 133 and the photographing direction of the imaging module 120 are related to each other, in the photographing state, and specifically, as shown in FIG. 3B, an arrangement direction of the first image sensor 122a and the second image sensor 122b of the imaging module 120 becomes a direction along the extension direction of the second shaft 133. Further, in the imaging module 120, the optical axis direction of the first image sensor 122a and the second image sensor 122b, that is, a direction in which there is the CP, becomes the photographing direction. Therefore, an extension direction of the second shaft 133 may be arbitrarily determined, so that the photographing direction of the imaging module 120 becomes a desired direction, in accordance with the shape or position of an affected part.

Further, in the first embodiment, the CP angle may be controlled in the imaging module 120, by having a rotation drive mechanism, such as a motor or an actuator, for example, included in the connection section 125 of the imaging module 120. In the case where a rotation drive mechanism is included in the connection section 125, this rotation driving may be controlled, for example, by the imaging module drive control section 440. For example, the imaging module drive control section 440 can control the rotation driving of the connection section 125 so that the imaging module 120 has a desired CP angle.

On the other hand, in the case of shifting from the photographing state to the storage state, in the photographing state shown in FIG. 3B, the imaging module connection section 130 and the imaging module 120 are pulled towards the inside of the lens barrel 110, in the negative direction of the X axis, by the imaging module drive section 140. Note that, the imaging module drive section 140 may have a mechanism which adjusts the size of the tension in the elastic member 134, and may allow the size of the tension in the elastic member 134 to be reduced, when shifting from the photographing state to the storage state. Since the force which rotates the second shaft 133 by the elastic member 134 can be weakened, by reducing the size of the tension in the elastic member 134, it becomes possible to store the imaging module 120 within the lens barrel 110 more smoothly.

Heretofore, the storage state and the photographing state, in the endoscope 10 according to the first embodiment, has been described by referring to FIG. 3A and FIG. 3B. Here, a case has been described in FIG. 3A and FIG. 3B in which shifting is implemented between the storage state and the photographing state by using the elastic member 134. However, in the first embodiment, the method of shifting from the storage state to the photographing state is not limited to such an example. For example, as a modified example of the first embodiment, shifting may be implemented from the storage state to the photographing state, by having a rotation drive mechanism included in the joint section 132, for example. Such a modified example of the first embodiment will be described by referring to FIG. 4. FIG. 4 is an explanatory diagram for describing a schematic configuration of the endoscope 10 in a photographing state, according to a modified example of the first embodiment. Note that, for simplicity, only the endoscope 10, that is, the lens barrel 110, the imaging module 120, the imaging module connection section 130, and the imaging module drive section 140, from among the endoscope apparatus shown in FIG. 1, will be illustrated in FIG. 4, similar to that of FIG. 3A and FIG. 3B, and the constituent members other than these will be omitted in the illustration. Further, for simplicity, only the configuration of the lens barrel 110 and the imaging module connection section 130 near to this distal end will be illustrated in FIG. 4. In addition, in order to describe the configuration of the imaging module 120 and the imaging module connection section 130 within the lens barrel 110, the outline of the lens barrel will be illustrated with only a dotted line. Here, FIG. 4 schematically shows a configuration of the endoscope 10 in a photographing state, and the dimensions or the like of each constituent member is not limited to the example shown in FIG. 4. Further, the X axis and the Y axis in FIG. 4 are defined similar to those in FIG. 3A and FIG. 3B.

With reference to FIG. 4, in the endoscope 10 according to the present modified example in a photographing state, the joint section 132 has a drive mechanism such as a motor or an actuator, for example, and the second shaft 133 can be allowed to rotate with respect to the first shaft 131, by this drive mechanism. Further, the rotation driving in the joint section 132 may be controlled by the imaging module drive control section 440.

In the example shown in FIG. 3B, since the second shaft 133 is allowed to rotate with respect to the first shaft 131 by the tension of the elastic member 134, it can only perform rotation in one direction determined in advance. On the other hand, in the modified example shown in FIG. 4, since the second shaft 133 is allowed to rotate with respect to the first shaft 131 by the rotation drive mechanism of the joint section 132, the imaging module 120 can be allowed to project in an arbitrary direction, in the range the joint section 132 is capable of rotating. For example, when the second shaft 133 is set so as to be capable of freely rotating within the X-Y plane shown in FIG. 4 (the plane on which the X axis and the Y axis are provided), it is possible for the rotation drive mechanism of the joint section 132 to set the negative direction of the X axis as the photographing direction, such as shown in FIG. 4. Therefore, according to the present modified example, it becomes possible to change the direction of the imaging module 120 while the position of the lens barrel 110 itself is fixed, and it becomes possible to photograph with a greater degree of freedom, such as photographing a state of the rear side of an internal organ, for example.

Heretofore, a configuration of the imaging module 120 and the endoscope 10 according to the first embodiment has been described by referring to FIG. 2A to FIG. 2D, FIG. 3A, and FIG. 3B. Here, it is preferable that a configuration of the imaging module 120 and the endoscope 10 is designed by considering the following points.

Firstly, since it may be necessary for the imaging module 120 to be stored within the lens barrel 110 in the storage state, a size of the imaging module 120 is sought after which is a size capable of being stored in the lens barrel 110. Here, in an endoscope which generally photographs 2D images, the diameter of this lens barrel is approximately several mm, for example. When considering the physical burden on a person under measurement, it is not preferable for the diameter of the lens barrel to be larger than this size.

Secondly, in the case where 3D images are to be photographed by the imaging module 120, the first imaging section 120*a* and the second imaging section 120*b* each acquire so-called images for the left eye and the right eye, such as described above. Therefore, it is preferable that the first imaging section 120*a* and the second imaging section 120*b*, and consequently each of the elements installed in in the first imaging section 120*a* and the second imaging section 120*b*, be symmetrically aligned in the imaging module 120.

Thirdly, in the case where 3D images are to be photographed in the imaging module 120, the interval between the first image sensor 122*a* and the second image sensor 122*b* becomes an important factor for determining this photographing range. Further, as described above, since the interval between the first image sensor 122*a* and the second image sensor 122*b* influences the CP distance, this interval will also be a factor for determining a zero point. Therefore, it is preferable that an appropriate design is made for the interval between the first image sensor 122*a* and the second image sensor 122*b*, in accordance with the purpose or the like of the endoscope 10.

Fourthly, by considering that inside the body cavity of a human is dark, it is preferable that the first light source 123*a* and the second light source 123*b* are arranged so that light without unevenness is incident on the first image sensor 122*a* and the second image sensor 122*b*.

In the present embodiment, a configuration of the imaging module 120 and the endoscope 10 has been determined, such as shown in FIG. 2A to FIG. 2D, FIG. 3A, FIG. 3B and FIG. 4, upon considering the four points described above. That is, for the first point, each of the elements on the first substrate 121*a* and the second substrate 121*b* are arranged in one row in the imaging module 120. Further, the imaging module 120 is stored within the lens barrel 110, so that an arrangement direction of each of these elements becomes a direction along the extension direction of the lens barrel 110. Therefore, it may not be necessary for the diameter of the lens barrel 110 to be generally changed from the size of a lens barrel in an endoscope for 2D images, for example.

Further, for the second point, as shown in FIG. 2A to FIG. 2D, the first imaging section 120*a* and the second imaging section 120*b* are arranged in the imaging module 120 so as to symmetrically sandwich the connection section 125.

Further, for the third point, as shown in FIG. 2A to FIG. 2D, in the imaging module 120, the first image sensor 122*a* and the second image sensor 122*b* are supported by being integrally incorporated into one imaging module 120. In the technology disclosed in the above described JP S63-294508A and JP H4-500768A, a pair of image sensors for obtaining 3D images project from mutually different positions of the lens barrel, as mutually different mechanisms. Therefore, there is the possibility that the distance between the pair of imaging sections, or the angle formed by the imaging surfaces of these image sensors (the CP angle in the first embodiment and the second embodiment), deviates from a designed value, due to mechanical distortions or the like. In contrast to this, in the present embodiment, the first image sensor 122*a* and the second image sensor 122*b* are integrally incorporated into the imaging module 120. Therefore, the distance between the first image sensor 122a and the second image sensor 122b, or the CP angle, is fixed to a prescribed value more stably, and it becomes possible to acquire 3D images more stably.

Further, for the fourth point, as shown in FIG. 2A to FIG. 2D, a pair of light sources (the first light source 123a and the second light source 123b) is arranged in the imaging module 120 so as to sandwich the first image sensor 122a and the second image sensor 122b. Here, when considering the darkness inside the body cavity of the person under measurement, light sources which emit light with a high intensity are generally sought after as the light sources in the endoscope apparatus. Therefore, it may be necessary to use large-sized light sources in order to have a desired intensity as the output light, and there is a common configuration which guides light from these light sources up to the distal end of the endoscope by a light guiding unit such as optical fibers. On the other hand, in the present embodiment, as described above, image sensors with higher sensitivities are used, such as rear surface illumination type sensors, for example, as the first image sensor 122a and the second image sensor 122b. Therefore, in the present embodiment, even in the case where an intensity up to here may not be necessary from the output light of the light sources, and a small-sized light source such as an LED is used as the first light source 123a and the second light source 123b, it is possible to photograph clear images. Since a configuration using a light guiding unit such as optical fibers is generally expensive, the cost for the endoscope apparatus 1 can be reduced by using a comparatively cheaper light source such as an LED, such as in the present embodiment. Further, by restraining the number of light sources installed in the imaging module 120 to the minimum necessary number, the size of the imaging module 120 can be made smaller, and 3D images can be acquired without it being necessary to change the diameter of the lens barrel 110 from that of a general size. Note that, while a case has been described above in which the imaging module 120 has a pair of light sources (the first light source 123a and the second light source 123b), the present embodiment is not limited to such an example. For example, the light source included in the imaging module 120 may be one light source, or may be an arbitrary number of three or more light sources. By having the light sources included in the imaging module 120 irradiate uniform light to a region to be photographed, clear images of the region to be photographed may be photographed by the first image sensor 122a and the second image sensor 122b, and the number and arrangement position of the light sources may be arbitrary set.

2. The Second Embodiment

Next, a second embodiment of the present disclosure will be described by referring to FIG. 5A and FIG. 5B. Note that, in the second embodiment of the present disclosure, only the configuration of the endoscope is different from that of the first embodiment, and the other configuration, that is, the configuration of the apparatus body 20, is the same as that of the first embodiment. Therefore, in the following description for the second embodiment, a description will be omitted for the overlapping configuration, and the configuration of the endoscope, which is different from that of the first embodiment, will mainly be described.

[2-1. Configuration of the Endoscope (Storage State and Photographing State)]

A configuration of an endoscope 30 according to the second embodiment will be described in detail by referring to FIG. 5A and FIG. 5B. With reference to FIG. 5A and FIG. 5B, the endoscope 30 according to the second embodiment has a lens barrel 110, an imaging module 160, an imaging module connection section 150, and an imaging module drive section 140. Here, since the functions and configurations of the lens barrel 110 and the imaging module drive section 140, from among the constituent members of the endoscope 30, are both the same as the functions and configurations of the corresponding constituent members of the endoscope 10 according to the first embodiment, a detailed description of them will be omitted. Hereinafter, the functions and configurations of the imaging module 160 and the imaging module connection section 150, which are different from those of the first embodiment, will be described in detail, along with a storage state and a photographing state of the imaging module 160 in the second embodiment, by referring to FIG. 5A and FIG. 5B. Here, the imaging module 160 and the imaging module connection section 150 correspond to the imaging module 120 and the imaging module connection section 130, respectively, in the first embodiment. Note that, for simplicity, only the configuration of the lens barrel 110 and the imaging module connection section 150 near to this distal end will be illustrated in the endoscope 30 shown in FIG. 5A and FIG. 5B. In addition, in order to describe the configuration of the imaging module 160 and the imaging module connection section 150 within the lens barrel 110, the outline of the lens barrel will be illustrated with only a dotted line. Here, FIG. 5A and FIG. 5B schematically show a configuration of the endoscope 30 in a storage state and in a photographing state, and the dimensions or the like of each constituent member is not limited to the example shown in FIG. 5A and FIG. 5B. Further, in FIG. 5A and FIG. 5B, the extension direction of the lens barrel 110 is defined as an X axis, and additionally, the distal end direction of the lens barrel 110 is defined as a positive direction of the X axis.

First, a configuration of the imaging module 160 according to the second embodiment will be described by referring to FIG. 5A and FIG. 5B. The imaging module 160 has a first imaging section 160a and a second imaging section 160b, and is constituted by combining this first imaging section 160a and this second imaging section 160b via a connection section 165.

Here, the configurations of the first imaging section 160a and the second imaging section 160b are the same as the configurations of the first imaging section 120a and the second imaging section 120b of the imaging module 120 according to the first embodiment. That is, the first imaging section 160a has a first substrate 121a, a first image sensor 122a, a first light source 123a, and a first cable connector part 124a. Further, the second imaging section 160b has a second substrate 121b, a second image sensor 122b, a second light source 123b, and a second cable connector part 124b. Also, the first imaging section 160a and the second imaging section 160b are combined in the imaging module 160 so as to symmetrically sandwich the connection section 165. That is, the imaging module 160 is different with respect to the imaging module 120 according to the first embodiment in that it has the connection section 165 instead of the connection section 125, and the configurations other than this may be the same as those of the imaging module 120.

The connection section 165 rotatably connects the first imaging section 160a and the second imaging section 160b to each other, so that the imaging surface of the first image sensor 122a and the imaging surface of the second image sensor 122b face each other, around the connection section 165. Hereinafter, the function and configuration of the connection section 165 will be described in detail for the endoscope 30 according to the second embodiment in a storage state and a photographing state.

The endoscope 30 according to the second embodiment in a storage state will be described by referring to FIG. 5A. FIG. 5A is an explanatory diagram for describing a schematic configuration of the endoscope 30 according to the second embodiment in a storage state.

Figure 5A:
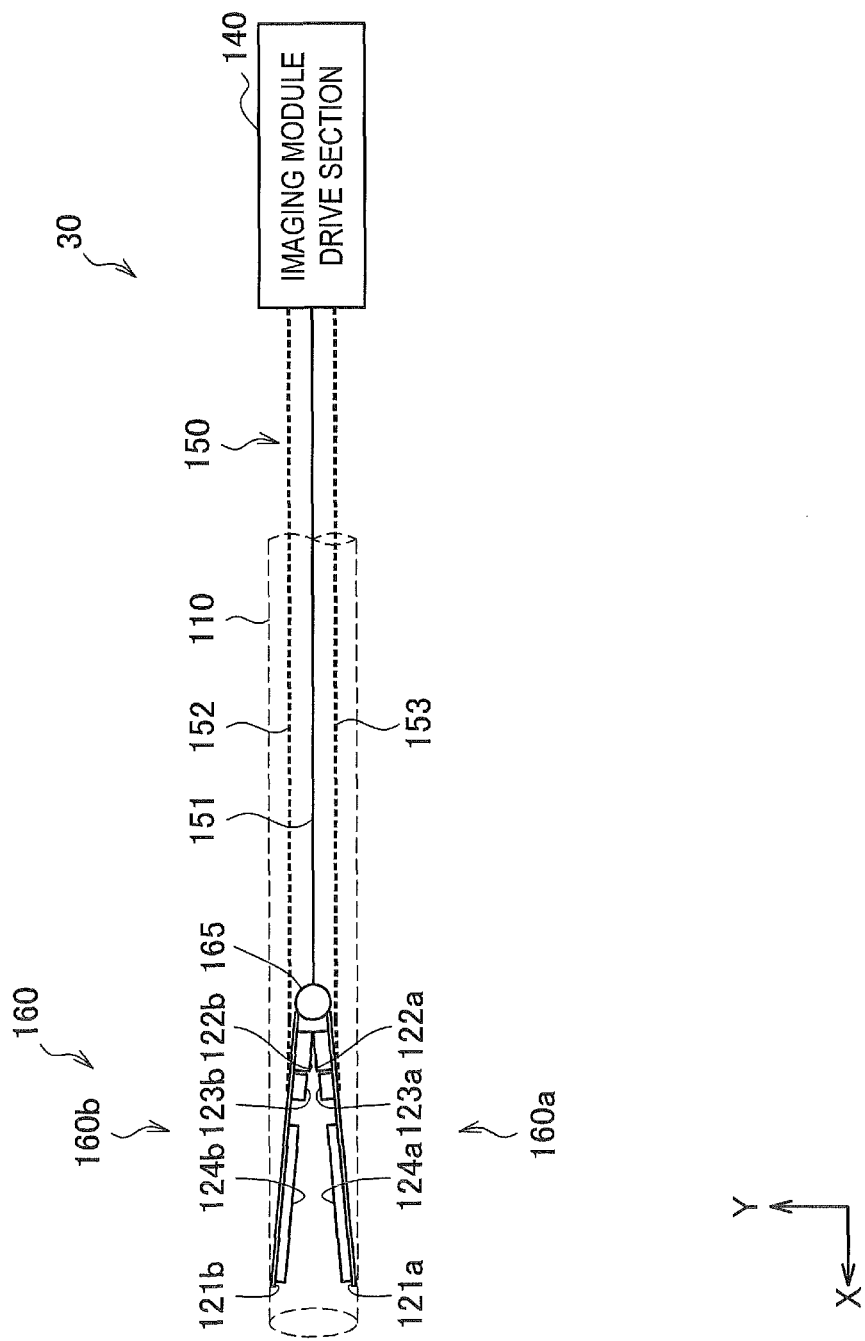
FIG. 5A is an explanatory diagram for describing a schematic configuration of an endoscope according to a second embodiment of the present disclosure in a storage state.

With reference to FIG. 5A, in the second embodiment, similar to that of the first embodiment, the imaging module 160 is stored within the lens barrel 110, in a storage state, so that an extension direction of the imaging surfaces of the first image sensor 122a and the second image sensor 122b becomes an extension direction of the lens barrel 110. Specifically, in a storage state in the second embodiment, the imaging module 160 may be folded and stored within the lens barrel 110 so that the first image sensor 122a and the second image sensor 122b mutually face each other, such as shown in FIG. 5A. More specifically, in the second embodiment, the imaging module 160 may be capable of mutually rotating the first imaging section 160a and the second imaging section 160b, by setting the connection section 165 as a rotation center, and may be stored within the lens barrel 110, by folding the first imaging section 160a and the second imaging section 160b so that the imaging surface of the first image sensor 122a and the imaging surface of the second image sensor 122b face each other, around the connection section 165. That is, in the storage state of the second embodiment, the imaging module 160 is stored within the lens barrel 110, by folding around the connection section 165 so that the CP angle becomes approximately 0 degrees. However, various elements are actually arranged on the surface sides of the first substrate 121a and the second substrate 121b of the imaging module 160, and since the CP angle becoming 0 degrees will be difficult, the imaging module 160 may be stored within the lens barrel 110 in a folded state, so that the CP angle is reduced in the range which can be stored in the lens barrel 110.

Further, the imaging module 160 is connected to the imaging module drive section 140, via the imaging module connection section 150 extending across the extension direction of the lens barrel 110 within the lens barrel 110. Here, the imaging module connection section 150 has a shaft 151 and a pair of elastic members 152 and 153.

One end of the shaft 151 is connected to the imaging module drive section 140, and this driving is controlled by the imaging module drive section 140. Specifically, for example, the imaging module drive section 140 can allow the shaft 151 to move in the X axis direction, by applying a force to the shaft 151 in the positive direction or the negative direction of the X axis. Further, the other end of the shaft 151 is connected to a partial region of the imaging module 160. For example, one end of the shaft 151 is connected to the connection section 165 on the rear side of the imaging module 120, such as shown in FIG. 5A. However, the position at which the shaft 151 is connected to the imaging module 160 is not limited to such an example, and this connection position is not limited if there are positions at which shifting is performed smoothly between the storage state and the photographing state.

Further, the pair of elastic members 152 and 153 extends between the imaging module drive section 140 and the imaging module 160, so as to extend along the shaft 151. Note that, the type of the elastic members 152 and 153 is not particularly limited, and elastic bodies of any type may be used. In the present embodiment, for example, the elastic members 152 and 153 are a pair of tension springs. Here, one end of each of the pair of elastic members 152 and 153 is connected to the rear surface of the first imaging section 160a and the second imaging section 160b of the imaging module 160, and a tension is applied in the direction of an increasing CP angle of the imaging module 160, that is, in the direction in which the folded imaging module 160 opens. However, as shown in FIG. 5A, by having the first imaging section 160a and the second imaging section 160b in the imaging module 160 hook onto the inner wall of the lens barrel 110, in the storage state, movement is restrained so that the imaging module 120 is opened by the elastic members 152 and 153. Here, in the following descriptions of FIG. 5A and FIG. 5B, in the case where the imaging module 160 is opened by the elastic members 152 and 153, a direction approximately equal to the arrangement direction of the first image sensor 122a and the second image sensor 122b in the imaging module 160 (a vertical direction within the figure) will be defined as a Y axis direction.

Next, the endoscope 30 according to the second embodiment in a photographing state will be described by referring to FIG. 5B. FIG. 5B is an explanatory diagram for describing a schematic configuration of the endoscope 30 according to the second embodiment in a photographing state.

With reference to FIG. 5B, in the second embodiment, the imaging module 160 is projected outside of the lens barrel 110, in a photographing state, so that an extension direction of the imaging surfaces of the first image sensor 122a and the second image sensor 122b becomes a direction along a direction different from the extension direction of the lens barrel 110. Specifically, as shown in FIG. 5B, the imaging module 160 may be projected from the lens barrel 110, so that the arrangement direction of the first image sensor 122a and the second image sensor 122b of the imaging module 160 becomes a direction along a direction approximately orthogonal to the extension direction of the lens barrel 110 (the Y axis direction).

In the case of shifting from the storage state to the photographing state, in the storage state shown in FIG. 5A, the imaging module connection section 150 and the imaging module 160 are pushed out from within the lens barrel 110 in the positive direction of the X axis, by the imaging module drive section 140. Since the restraint of the force which allows the imaging module 160 to be opened by the elastic members 152 and 153 will disappear when the imaging module 160 is completely projected outside from the lens barrel 110, the first imaging section 160a and the second imaging section 160b are mutually rotated so that the imaging module 160 opens around the connection section 165, that is, so that the photographing direction of the first image sensor 122a and the second image sensor 122b becomes a positive direction of the X axis, and shifts to the photographing state. Here, for example, a stopper mechanism, which limits the rotation of the first imaging section 160a and the second imaging section 160b up to a prescribed angle, is included in the connection section 165, and performs a control so that the imaging module 160 has a prescribed CP angle in the photographing state. Further, the tension of the elastic members 152 and 153 may be adjusted so that the imaging module 160 has a prescribed CP angle in the photographing state. Note that, in the present embodiment, a direction in which the elastic members 152 and 153 open the imaging module 160, that is, the arrangement direction of the first image sensor 122a and the second image sensor 122b in the imaging module 160, may be any direction if a direction different from the extension direction of the lens barrel 110, and is not limited to the example shown in FIG. 5B. In the present embodiment, the direction in which the elastic members 152 and 153 open the imaging module 160 may be arbitrarily determined, so that the photographing direction of the imaging module 160 becomes a desired direction, in accordance with the shape or position of an affected part.

On the other hand, in the case of shifting from the photographing state to the storage state, in the photographing state shown in FIG. 5B, the imaging module connection section 150 and the imaging module 160 are pulled towards the inside of the lens barrel 110, in the negative direction of the X axis, by the imaging module drive section 140. Note that, the imaging module drive section 140 may have a mechanism which adjusts the tension in the elastic members 152 and 153, and may allow the size of the tension in the elastic members 152 and 153 to be reduced, when moving from the photographing state to the storage state. Since the force which opens the imaging module 160 by the elastic members 152 and 153 can be weakened, by reducing the size of the tension in the elastic members 152 and 153, it becomes possible to store the imaging module 160 within the lens barrel 110 more smoothly.

Heretofore, the storage state and the photographing state, in the endoscope 30 according to the second embodiment, has been described by referring to FIG. 5A and FIG. 5B. Here, a case has been described in FIG. 5A and FIG. 5B in which shifting is implemented between the storage state and the photographing state by using the elastic members 152 and 153. However, in the second embodiment, the method of shifting between the storage state and the photographing state is not limited to such an example. For example, as a modified example of the second embodiment, shifting may be implemented between the storage state and the photographing state, by having a rotation drive mechanism, such as a motor or an actuator, for example, included in the connection section 165 of the imaging module 160. In the case where a rotation drive mechanism is included in the connection section 165, this rotation driving may be controlled, for example, by the imaging module drive control section 440. For example, the imaging module drive control section 440 can control the rotation driving of the connection section 165 so that the imaging module 160 has a desired CP angle. Therefore, for example, in the storage state, the imaging module drive control section 440 may control the rotation driving in the connection section 165 so that the CP angle becomes as small as possible, and in the photographing state, may perform a control which pushes the shaft 151 in the positive direction of the X axis, and may control the rotation driving in the connection section 165 so that the CP angle becomes an angle corresponding to a desired CP distance.

3. Conclusion

As described above, according to the first embodiment and the second embodiment of the present disclosure, the following effects are obtained.

First, according to the first embodiment and the second embodiment, each of the elements on the first substrate 121a and the second substrate 121b are arranged in one row in the imaging modules 120 and 160. Further, the imaging modules 120 and 160 are stored within the lens barrel 110, so that the arrangement direction of each of these elements becomes a direction along the extension direction of the lens barrel 110. Therefore, it may not be necessary for the diameter of the lens barrel 110 to be changed from the size of a lens barrel, for example, in an endoscope for 2D images (for example, a diameter of several mm)

Further, according to the first embodiment and the second embodiment, in the imaging modules 120 and 160, the first image sensor 122a and the second image sensor 122b are supported by being integrally incorporated into one of the imaging modules 120 and 160. In the technology disclosed in the above described JP S63-294508A and JP S63-294508A, a pair of imaging sections for obtaining 3D images project from mutually different positions of the lens barrel, as mutually different mechanisms. Therefore, there is the possibility that the distance between the pair of imaging sections, or the angle formed by the imaging surfaces of these image sensors (the CP angle in the first embodiment and the second embodiment), deviates from a designed value, due to mechanical distortions or the like. In contrast to this, in the first embodiment and the second embodiment, the first image sensor 122a and the second image sensor 122b are integrally incorporated into the imaging modules 120 and 160. Therefore, the distance between the first image sensor 122a and the second image sensor 122b, or the CP angle, is fixed to a prescribed value more stably, and it becomes possible to acquire 3D images more stably.

Here, for example, even in the case where the arrangement position of the pair of imaging sections for obtaining 3D images deviates from a prescribed position, it is possible to correct this deviation by software, for example, at the stage when an image signal process is performed. However, since the image signal amount performed by the control section 400 will increase when performing such a correction by software, there is the possibility that the imaging modules 120 and 160 photograph a region to be photographed, and thereafter the latency up to when this image is displayed on the display section 300 becomes large. An increase of such latency becomes an obstruction to perform intuitive operations by a user who performs the operations of the endoscopes 10 and 30 while referring to the images displayed on the display section 300. On the other hand, according to the first embodiment and the second embodiment, by having the first image sensor 122a and the second image sensor 122b integrally incorporated into the imaging modules 120 and 160, such as described above, a deviation of the arrangement position of the first image sensor 122a and the second image sensor 122b is not likely to occur. Therefore, stable 3D images are obtained without causing an increase of the above described latency.

Further, according to the first embodiment and the second embodiment, a pair of light sources (the first light source 123a and the second light source 123b) is arranged in the imaging modules 120 and 160, so as to sandwich the first image sensor 122a and the second image sensor 122b. In addition, image sensors with a higher sensitivity are used, such as a rear surface illumination type sensor, for example, as the first image sensor 122a and the second image sensor 122b. Therefore, even in the case where an intensity up to here may not be necessary from the output light of the light sources, and a small-sized light source such as an LED is used as the first light source 123a and the second light source 123b, it is possible to photograph clear images. Since a configuration using a light guiding unit such as optical fibers is generally expensive, the cost for the endoscope apparatus 1 can be reduced by using a comparatively cheaper light source such as an LED, such as in the present embodiment. Further, by restraining the number of light sources installed in the imaging modules 120 and 160 to the minimum necessary number, the size of the imaging modules 120 and 160 can be made smaller, and 3D images can be acquired without it being necessary to change the diameter of the lens barrel 110 from the size of a lens barrel in an endoscope generally used for 2D images (for example, a diameter of several mm).

Further, according to the first embodiment and the second embodiment, signals for 3D images are generated, based on image signals acquired by the imaging modules 120 and 160, and additionally, the CP distance in the imaging modules 120 and 160 is adjusted, based on these signals for 3D images, and an adjustment amount of the CP angle of the imaging modules 120 and 160 is calculated. Specifically, an adjustment amount of the CP angle for the CP to be positioned at an affected part (a region to be photographed) is calculated by the CP angle adjustment amount calculation section 430. Also, the CP angle of the imaging modules 120 and 160 is adjusted, based on this calculated adjustment amount. In this way, by having the CP angle of the imaging modules 120 and 160 adjusted so that the CP is positioned at an affected part (a region to be photographed), a zero point of the projection amount or depth amount in the 3D images is adjusted near to the affected part, and 3D images close to what is actually seen by the human eyes are displayed on the display section 300. Further, in this way, by having the CP angle of the imaging modules 120 and 160 capable of being adjusted, since it may become unnecessary for a plurality of imaging modules to be prepared in advance which have different CP angles in accordance with the distance between the imaging modules 120 and 160 and the region to be photographed (for example, a plurality of imaging modules with CP angles of 30 degrees, 45 degrees, 75 degrees or the like), it becomes possible to reduce the cost.

It should be understood by those skilled in the art that various modifications, combinations, sub-combinations and alterations may occur depending on design requirements and other factors insofar as they are within the scope of the appended claims or the equivalents thereof.

For example, in the present embodiment, by having the first light source 123a and the second light source 123b of the imaging module 120 each irradiate light of different wavelength bandwidths, and having the image signal processing section 410 perform a filtering process of specified wavelengths for the image signals, an observation of an affected part may be performed using a method of so-called NBI (Narrow Band Imaging) (registered trademark). By applying NBI to the endoscope apparatus 1 according to the present embodiment, it becomes possible to observe, with 3D images, the state of an affected part which is not able to be directly observed with the naked eye. Further, by combining with an enlargement function by the display control section 450, it becomes possible to observe an affected part with higher convenience.

Additionally, the present technology may also be configured as below.

(1) An endoscope including:
a lens barrel in which a partial region including at least a distal end is inserted inside a body cavity of a person under measurement; and
an imaging module provided in the distal end of the lens barrel, the imaging module has at least one pair of image sensors arranged in parallel at a mutually prescribed distance,
wherein the imaging module is switched between a storage state in which the imaging module is stored within the lens barrel in a manner that an extension direction of imaging surfaces of the image sensors becomes a direction along a first direction which is an extension direction of the lens barrel, and a photographing state in which the imaging module is projected outside of the lens barrel in a manner that the extension direction of the imaging surfaces of the image sensors becomes a direction along a second direction which is a direction different from the first direction.

(2) The endoscope according to (1),
wherein the imaging module is stored within the lens barrel, in the storage state, in a manner that an arrangement direction of the pair of image sensors becomes the direction along the first direction.

(3) The endoscope according to (1),
wherein the imaging module is folded and stored within the lens barrel, in the storage state, in a manner that the pair of image sensors face each other.

(4) The endoscope according to any one of (1) to (3),
wherein the pair of image sensors are arranged in parallel in a manner that a cross point angle formed by the imaging surfaces of the pair of image sensors becomes equal to or less than 180 degrees.

(5) The endoscope according to any one of (1) to (4),
wherein the imaging module further includes at least one pair of light sources, and
wherein the pair of light sources are arranged in one row with the pair of image sensors.

(6) The endoscope according to (5),
wherein the pair of light sources are arranged at positions sandwiching the pair of image sensors.

(7) The endoscope according to any one of (1) to (6),
wherein the imaging module includes a rotation mechanism, between the pair of image sensors, which sets a direction perpendicular to an arrangement direction of the pair of image sensors and parallel to the imaging surfaces of the pair of image sensors as a rotation axis direction,
wherein the pair of image sensors are capable of being mutually rotated by the rotation mechanism, and
wherein a cross point angle formed by the imaging surfaces of the pair of image sensors is adjusted by the rotation mechanism.

(8) An endoscope apparatus including:
an endoscope including a lens barrel in which a partial region including at least a distal end is inserted inside a body cavity of a person under measurement, and an imaging module provided in the distal end of the lens barrel, the imaging module including at least one pair of image sensors arranged in parallel at a mutually prescribed distance and being switched between a storage state in which the imaging module is stored within the lens barrel in a manner that an extension direction of imaging surfaces of the image sensors becomes a direction along a first direction which is an extension direction of the lens barrel, and a photographing state in which the imaging module is projected outside of the lens barrel in a manner that the extension direction of the imaging surfaces of the image sensors becomes a direction along a second direction which is a direction different from the first direction; and
an imaging module drive control section which controls at least the switching between the storage state and the photographing state in the imaging module.

(9) The endoscope apparatus according to (8),
wherein the imaging module includes a rotation mechanism, between the pair of image sensors, which sets a direction perpendicular to an arrangement direction of the pair of image sensors and parallel to the imaging surfaces of the pair of image sensors as a rotation axis direction,
wherein the pair of image sensors are capable of being mutually rotated by the rotation mechanism, and wherein the imaging module drive control section additionally controls a cross point angle formed by the imaging surfaces of the pair of image sensors in the imaging module by driving the rotation mechanism to rotate.

(10) The endoscope apparatus according to (9), further including:
a cross point angle adjustment amount calculation section which calculates an adjustment amount of the cross point angle, in a case where a cross point of an intersection point where straight lines orthogonal to the imaging surfaces of the pair of image sensors intersect each other is positioned in a region to be photographed, based on image signals acquired by the pair of image sensors,
wherein the imaging module drive control section controls the cross point angle, during photography inside the body cavity of the person under measurement, based on the calculated adjustment amount.

(11) The endoscope apparatus according to any one of (8) to (10), further including:
a three-dimensional image signal generation section which generates an image signal for displaying inside of the body cavity of the person under measurement as a three-dimensional image based on image signals acquired by the pair of image sensors.

What is claimed is:

1. An endoscope comprising:
a lens barrel in which a partial region including at least a distal end is configured to be inserted inside a body cavity of a person under measurement;
an imaging module projected outside of the distal end of the lens barrel of the endoscope, the imaging module including:
a pair of substrates symmetrically arranged about a rotation mechanism of a connection section, and
a pair of image sensors symmetrically arranged at a predetermined distance from the connection section, wherein each substrate of the pair of substrates includes an image sensor of the pair of image sensors; and
an imaging module connection section including a first shaft, a second shaft, and a rotation section disposed between the first shaft and the second shaft, the second shaft being disposed between the connection section and the rotation section, the first shaft extending into the lens barrel,
wherein,
the pair of substrates are configured to be rotated by the rotation mechanism about the connection section,
the second shaft is configured to be rotated about the rotation section,
the imaging module is configured to stereoscopically image an object from an imaging direction that is different from an insertion direction in which the pair of image sensors move through a portion of the lens barrel toward the distal end of the lens barrel, and
a cross point angle formed by imaging surfaces of the pair of image sensors is adjusted by the rotation mechanism.

2. The endoscope according to claim 1, wherein the pair of image sensors is arranged in a manner such that a cross point angle formed by imaging surfaces of the pair of image sensors is equal to or less than 180 degrees.

3. The endoscope according to claim 1,
wherein the imaging module further includes at least one pair of light sources, and
wherein the pair of light sources is arranged in one row with the pair of image sensors.

4. The endoscope according to claim 3, wherein the pair of light sources is arranged at positions sandwiching the pair of image sensors.

5. The endoscope according to claim 1, wherein imaging surfaces of the image sensors face a direction that is opposite to a direction in which the lens barrel is inserted into the body cavity.

6. An endoscope apparatus comprising:
an endoscope including:
a lens barrel in which a partial region including at least a distal end is configured to be inserted inside a body cavity of a person under measurement,
an imaging module projected outside of the distal end of the lens barrel of the endoscope, the imaging module including a pair of substrates symmetrically arranged about a rotation mechanism of a connection section, and a pair of image sensors symmetrically arranged at a predetermined distance from the connection section, wherein each substrate of the pair of substrates includes an image sensor of the pair of image sensors, and
an imaging module connection section including a first shaft, a second shaft, and a rotation section disposed between the first and second shaft, the second shaft being disposed between the connection section and the rotation section, the first shaft extending into the lens barrel,
wherein,
the pair of substrates are configured to be rotated by the rotation mechanism about the connection section,
the second shaft is configured to be rotated about the rotation section,
the imaging module is configured to stereoscopically image an object from an imaging direction that is different from an insertion direction in which the pair of image sensors move through a portion of the lens barrel toward the distal end of the lens barrel, and
a cross point angle formed by imaging surfaces of the pair of image sensors is adjusted by the rotation mechanism, and
an imaging module drive control section which controls switching between a storage state and a photographing state in the imaging module.

7. The endoscope apparatus according to claim 6, further comprising:
a cross point angle adjustment amount calculation section which calculates an adjustment amount of the cross point angle based on image signals acquired by the pair of image sensors, wherein a cross point of an intersection point where straight lines orthogonal to imaging surfaces of the pair of image sensors intersect each other is positioned in a region to be photographed based on the image signals acquired by the pair of image sensors, and
wherein the imaging module drive control section controls the cross point angle, during photography inside the body cavity of the person under measurement, based on the calculated adjustment amount.

8. The endoscope apparatus according to claim 6, further comprising:
a three-dimensional image signal generation section which generates an image signal for displaying an inside of the body cavity of the person under measurement as a three-dimensional image based on image signals acquired by the pair of image sensors.

9. An endoscope comprising:
a lens barrel in which a partial region including at least a distal end is configured to be inserted inside a body cavity of a person under measurement;
an imaging module provided in the distal end of the lens barrel, the imaging module including:
- a pair of substrates symmetrically arranged about a rotation mechanism of a connection section, and
- a pair of image sensors symmetrically arranged at a predetermined distance from the connection section, wherein each substrate of the pair of substrates includes an image sensor of the pair of image sensors;

an imaging module connection section including a first shaft, a second shaft, and a rotation section disposed between the first shaft and the second shaft, the second shaft being disposed between the connection section and the rotation section, the first shaft extending into the lens barrel,
wherein,
  the pair of substrates are configured to be rotated by the rotation mechanism about the connection section,
  the second shaft is configured to be rotated about the rotation section, and
  a cross point angle formed by imaging surfaces of the pair of image sensors is adjusted by the rotation mechanism,
wherein the imaging module is switched between a storage state in which the imaging module is stored in a closed position within the lens barrel in a manner such that imaging surfaces of the image sensors extend substantially in a direction that is a longitudinal extension direction of the lens barrel and the imaging surfaces of the image sensors face a direction that is substantially orthogonal to the longitudinal extension direction of the lens barrel, and a photographing state in which the imaging module is projected outside of the lens barrel in an open position in a manner such that the imaging surfaces of the image sensors extend substantially in a direction that is different from the direction that is the longitudinal extension direction of the lens barrel.

* * * * *